United States Patent [19]
Melling et al.

[11] Patent Number: 5,820,009
[45] Date of Patent: Oct. 13, 1998

[54] ARTICULATED SURGICAL INSTRUMENT WITH IMPROVED JAW CLOSURE MECHANISM

[75] Inventors: Hugh Melling, Harbor Springs; Christopher L. Johnson, Plainwell; Jeffrey R. Oberlin, Augusta, all of Mich.

[73] Assignee: Richard-Allan Medical Industries, Inc., Richland, Mich.

[21] Appl. No.: 603,998

[22] Filed: Feb. 20, 1996

[51] Int. Cl.$^6$ ................................................ A61B 17/068
[52] U.S. Cl. ..................... 227/176.1; 227/1.9; 227/178.1
[58] Field of Search .................. 227/19, 178.1, 227/179.1, 175.1, 176.1, 180.1

[56] References Cited

U.S. PATENT DOCUMENTS

| | | |
|---|---|---|
| 960,300 | 6/1910 | Fischer . |
| 2,344,071 | 3/1944 | Wilson et al. ............................... 1/49.1 |
| 2,507,710 | 5/1950 | Grasso .................................... 128/312 |
| 2,518,994 | 8/1950 | Miller ..................................... 128/321 |
| 2,891,250 | 6/1959 | Hirata ............................................ 1/50 |
| 3,079,606 | 3/1963 | Bobrov et al. ............................... 1/120 |
| 3,082,426 | 3/1963 | Miles ........................................... 1/349 |
| 3,269,630 | 8/1966 | Fleischer .................................. 227/107 |
| 3,490,675 | 1/1970 | Green et al. .............................. 227/19 |

(List continued on next page.)

FOREIGN PATENT DOCUMENTS

| | | |
|---|---|---|
| 0324635A1 | 1/1989 | European Pat. Off. ......... A61B 17/10 |
| 0593920A1 | 9/1993 | European Pat. Off. ...... A61B 17/072 |
| 0625335A1 | 4/1994 | European Pat. Off. ...... A61B 17/072 |
| 0646357A1 | 9/1994 | European Pat. Off. ......... A61B 17/28 |
| 0668057A2 | 2/1995 | European Pat. Off. ......... A61B 17/28 |
| 0674876A2 | 3/1995 | European Pat. Off. ...... A61B 17/012 |
| 1237035 | 6/1960 | France . |
| 2437820 | 6/1979 | France .......................... A61B 17/12 |
| 869388 | 3/1953 | Germany . |
| 869527 | 3/1953 | Germany . |
| 728848 | 4/1980 | U.S.S.R. ........................ A61B 17/11 |
| 1452185 | 5/1974 | United Kingdom .......... A61B 17/42 |
| PCT/US93/ 01108 | 2/1993 | WIPO ......................... A61B 17/115 |

*Primary Examiner*—Scott A. Smith
*Attorney, Agent, or Firm*—Howard & Howard

[57] ABSTRACT

This invention provides an articulated surgical instrument for use in laparoscopic surgical procedures including, in general, a handle, an elongated shaft, and a tip. The shaft is coupled to the handle, and the tip is pivotally coupled to the distal end of the shaft for articulation about an articulation axis. The tip includes two opposed jaws. The jaws are pivotally coupled at a pivot axis for movement between an open position and a closed position, and at least one of the jaws has a camming portion proximal to the pivot axis of the jaws. The instrument further includes a camming driver disposed in the shaft for reciprocating movement between a proximal position and a distal position. The camming driver has a camming portion. The drive camming portion contacts the jaw camming portion at a cam point. Preferably, the jaw camming portion is a hemispherically-shaped projection and the driver camming portion is a ramp. Movement of the camming driver from its proximal position to its distal position causes the jaws to pivot from their open position to their closed positions.

21 Claims, 21 Drawing Sheets

U.S. PATENT DOCUMENTS

| | | | |
|---|---|---|---|
| 3,499,591 | 3/1970 | Green | 227/76 |
| 3,777,538 | 12/1973 | Weatherly et al. | 72/410 |
| 3,795,034 | 3/1974 | Strekopytov et al. | 29/212 D |
| 4,111,206 | 9/1978 | Vishnevsky et al. | 128/305 |
| 4,241,861 | 12/1980 | Fleischer | 227/135 |
| 4,243,047 | 1/1981 | Olsen | 128/751 |
| 4,244,372 | 1/1981 | Kapitanov et al. | 128/334 |
| 4,273,129 | 6/1981 | Boebel | 128/326 |
| 4,296,881 | 10/1981 | Lee | 227/30 |
| 4,304,236 | 12/1981 | Conta et al. | 128/325 |
| 4,354,628 | 10/1982 | Green | 227/19 |
| 4,383,634 | 5/1983 | Green | 227/19 |
| 4,429,695 | 2/1984 | Green | 128/305 |
| 4,473,077 | 9/1984 | Noiles et al. | 128/305 |
| 4,485,817 | 12/1984 | Swiggett | 128/334 |
| 4,488,523 | 12/1984 | Shichman | 128/334 |
| 4,522,206 | 6/1985 | Whipple et al. | 128/312 |
| 4,530,453 | 7/1985 | Green | 227/19 |
| 4,566,620 | 1/1986 | Green et al. | 227/19 |
| 4,576,167 | 3/1986 | Noiles | 128/334 |
| 4,608,981 | 9/1986 | Rothfuss et al. | 128/305 |
| 4,610,383 | 9/1986 | Rothfuss et al. | 227/19 |
| 4,646,751 | 3/1987 | Maslanka | 128/751 |
| 4,671,445 | 6/1987 | Barker et al. | 227/19 |
| 4,763,669 | 8/1988 | Jaeger | 128/751 |
| 4,784,137 | 11/1988 | Kulik et al. | 128/334 |
| 4,802,614 | 2/1989 | Green et al. | 227/19 |
| 4,991,764 | 2/1991 | Mericle | 227/178 |
| 5,040,715 | 8/1991 | Green et al. | 227/176 |
| 5,074,454 | 12/1991 | Peters | 227/178 |
| 5,100,042 | 3/1992 | Gravener et al. | 227/176 |
| 5,137,198 | 8/1992 | Nobis et al. | 227/19 |
| 5,170,925 | 12/1992 | Madden et al. | 227/175 |
| 5,190,203 | 3/1993 | Rodak | 227/175 |
| 5,240,163 | 8/1993 | Stein et al. | 227/175 |
| 5,307,976 | 5/1994 | Olson et al. | 227/178 |
| 5,312,023 | 5/1994 | Green et al. | 227/175 |
| 5,318,221 | 6/1994 | Green et al. | 227/178 |
| 5,327,908 | 7/1994 | Gerry | 128/774 |
| 5,330,502 | 7/1994 | Hassler et al. | 606/205 |
| 5,336,232 | 8/1994 | Green et al. | 606/151 |
| 5,337,937 | 8/1994 | Remiszewski et al. | 227/182 |
| 5,376,095 | 12/1994 | Ortiz | 606/143 |
| 5,403,342 | 4/1995 | Tovey et al. | 606/205 |
| 5,423,471 | 6/1995 | Mastri et al. | 227/181 |
| 5,425,737 | 6/1995 | Burbank et al. | 606/144 |
| 5,433,721 | 7/1995 | Hooven et al. | 606/143 |
| 5,449,365 | 9/1995 | Green et al. | 606/142 |
| 5,452,836 | 9/1995 | Huitema et al. | 227/176 |
| 5,456,684 | 10/1995 | Schmidt et al. | 606/41 |
| 5,478,003 | 12/1995 | Green et al. | 227/176 |
| 5,485,952 | 1/1996 | Fontayne | 227/178.1 |
| 5,507,426 | 4/1996 | Young et al. | 227/19 |
| 5,540,375 | 7/1996 | Bolanos et al. | 227/178.1 |

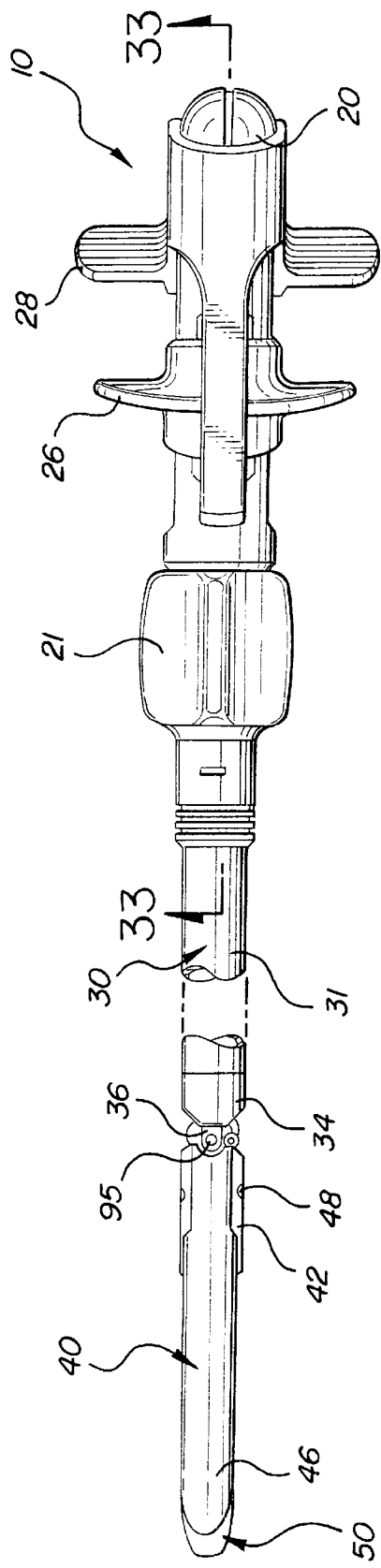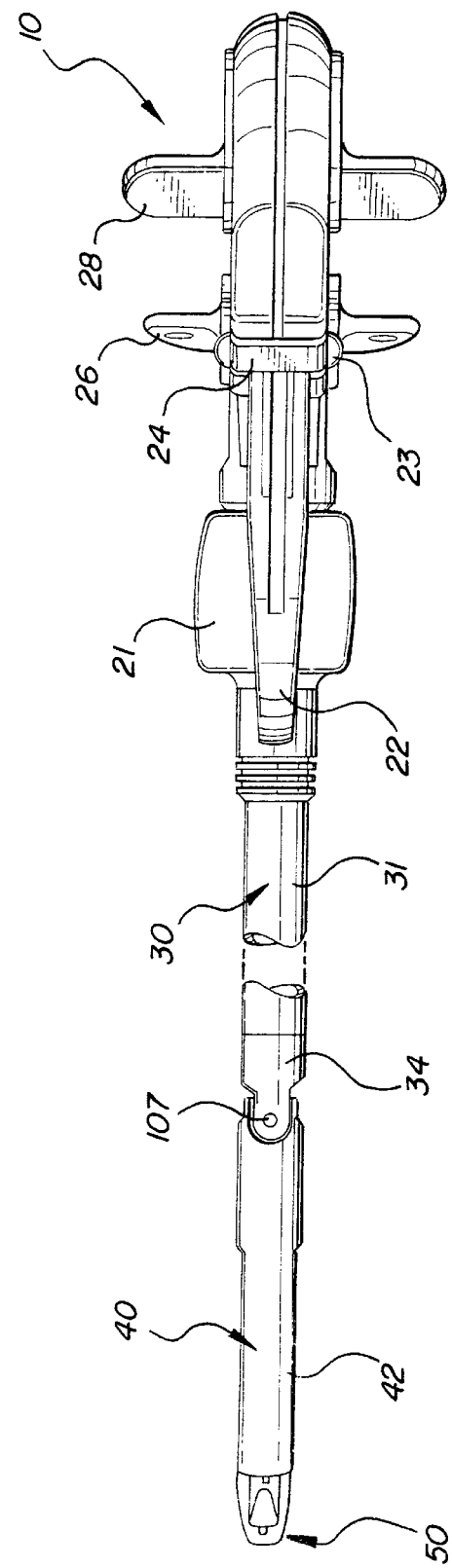

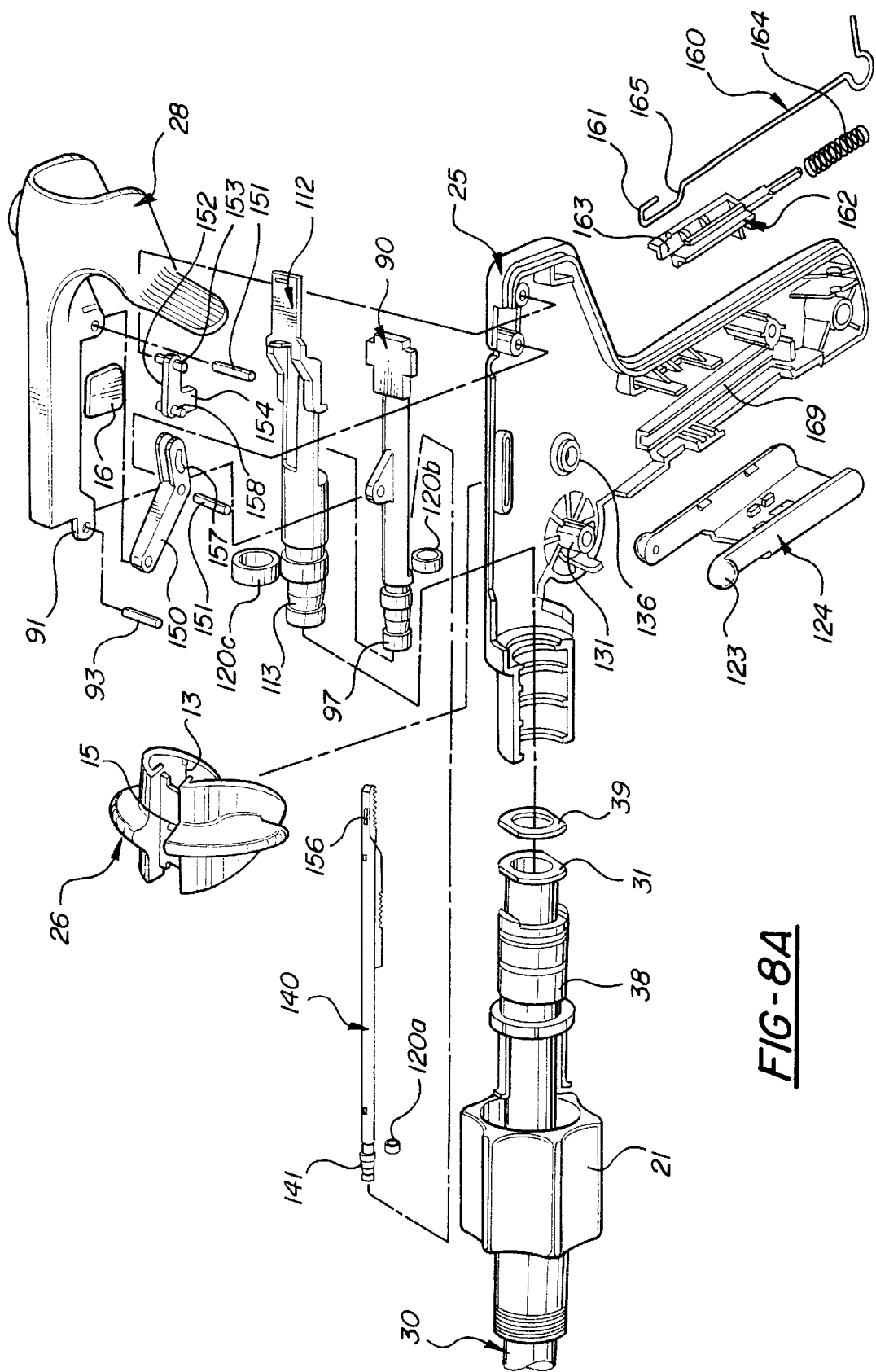

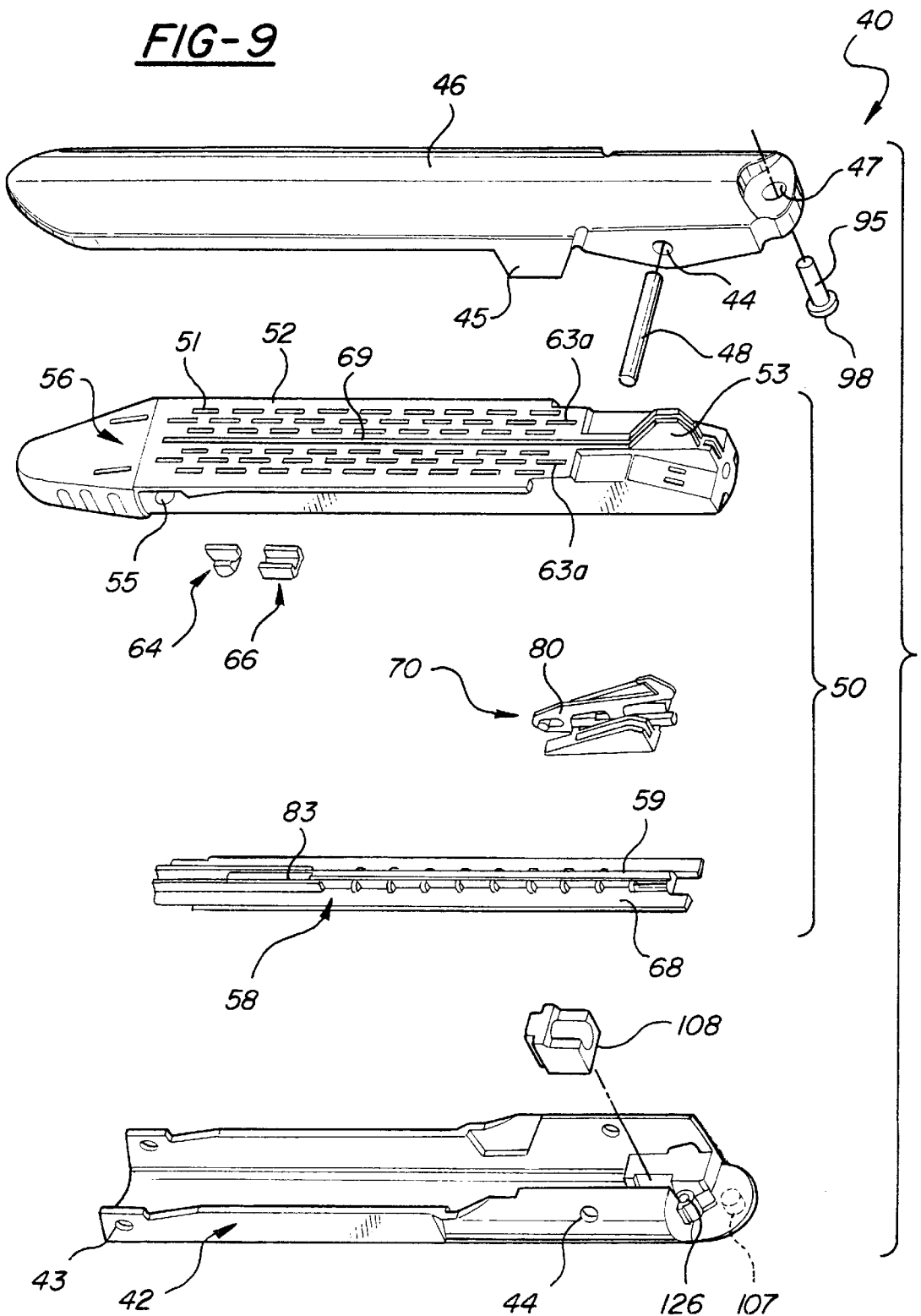

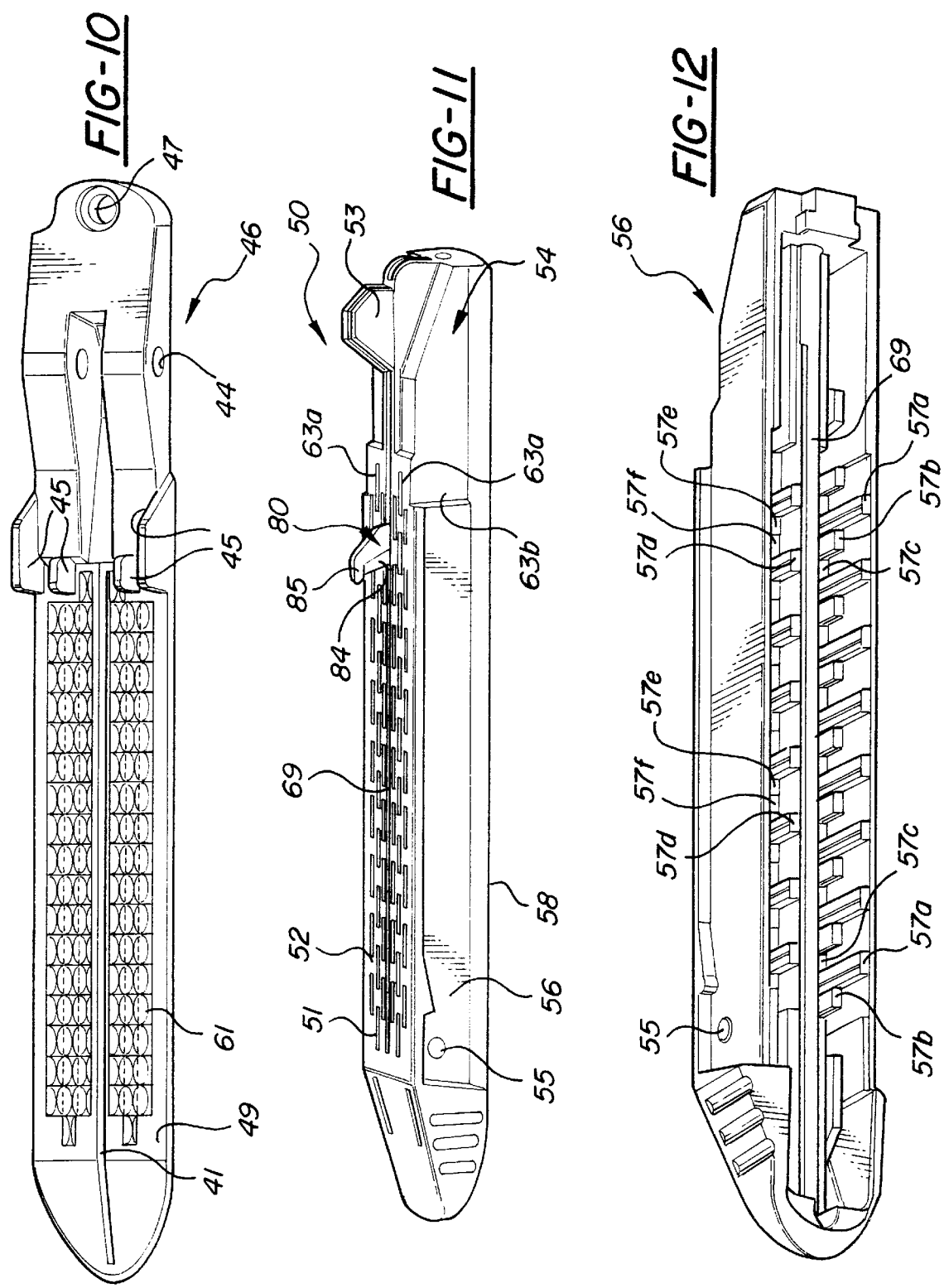

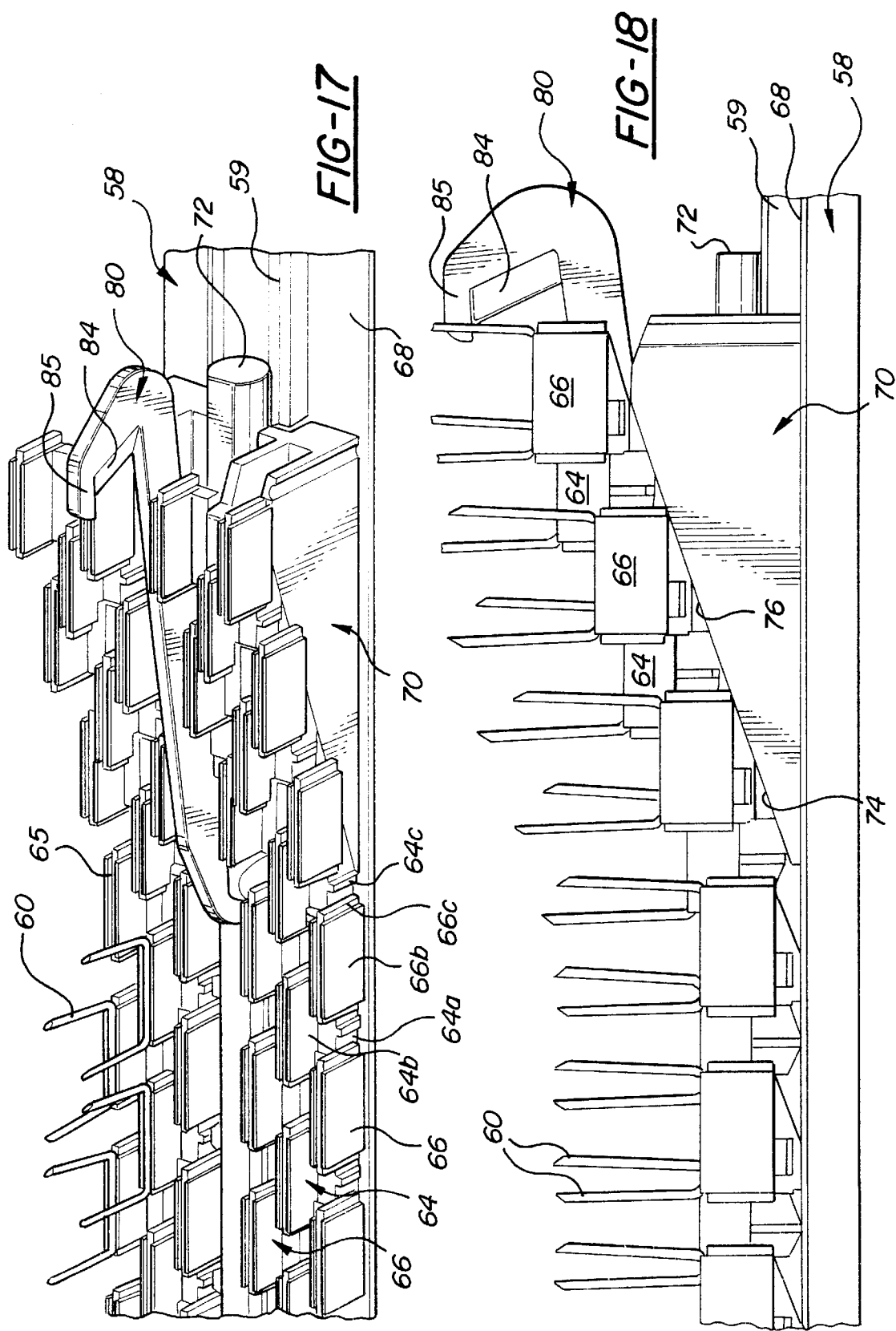

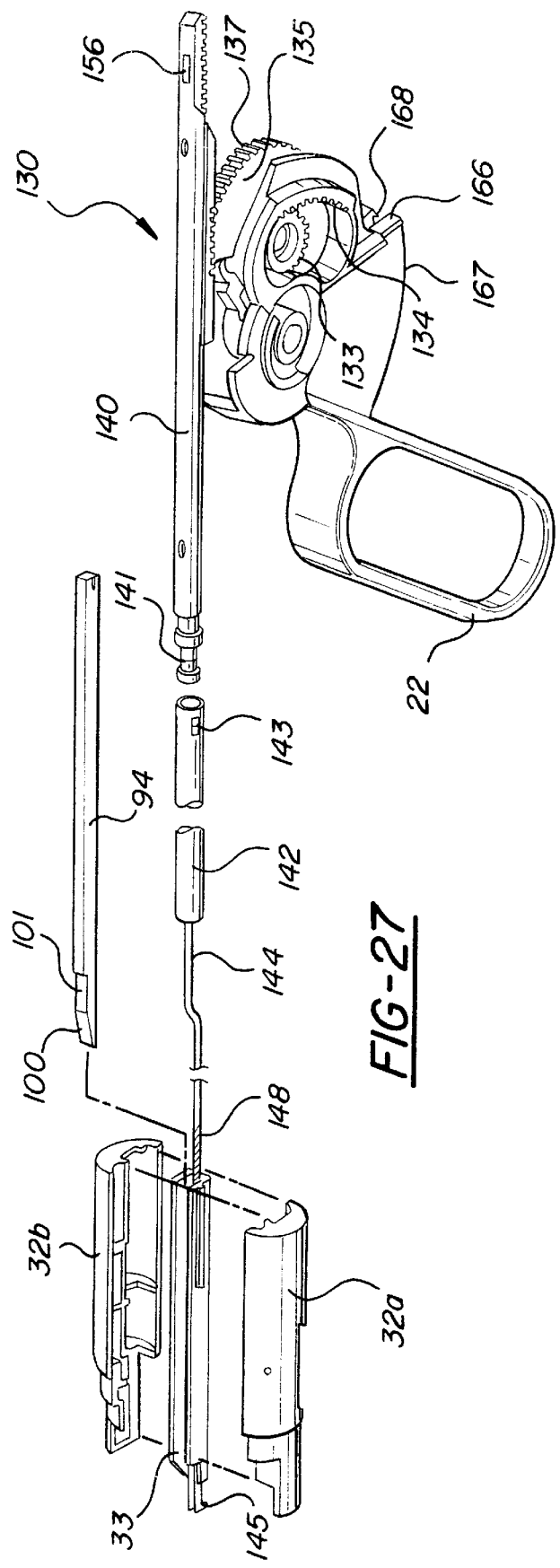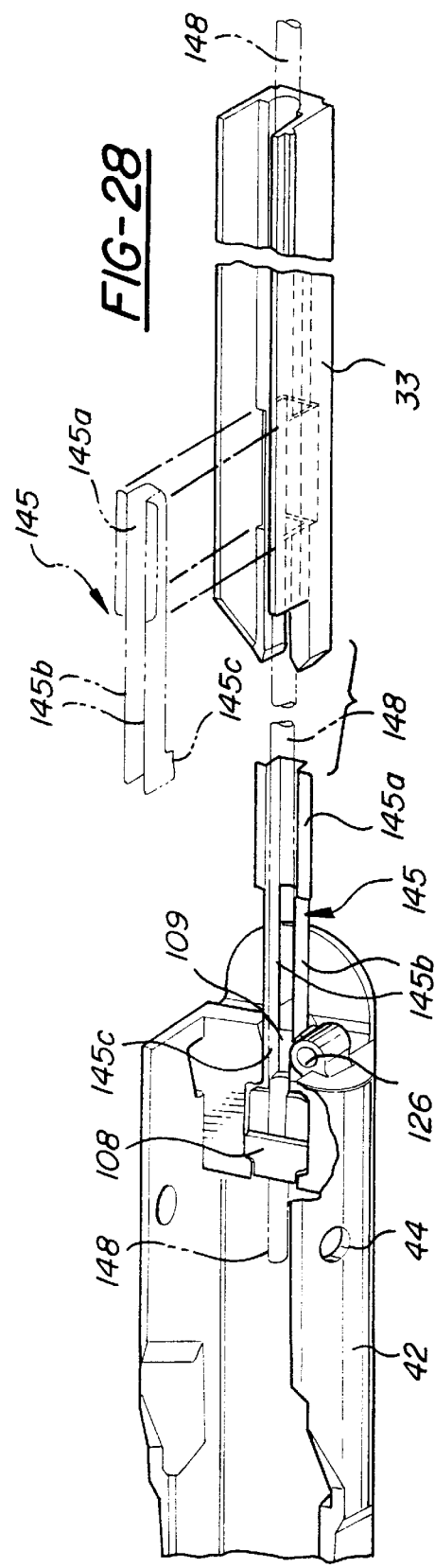

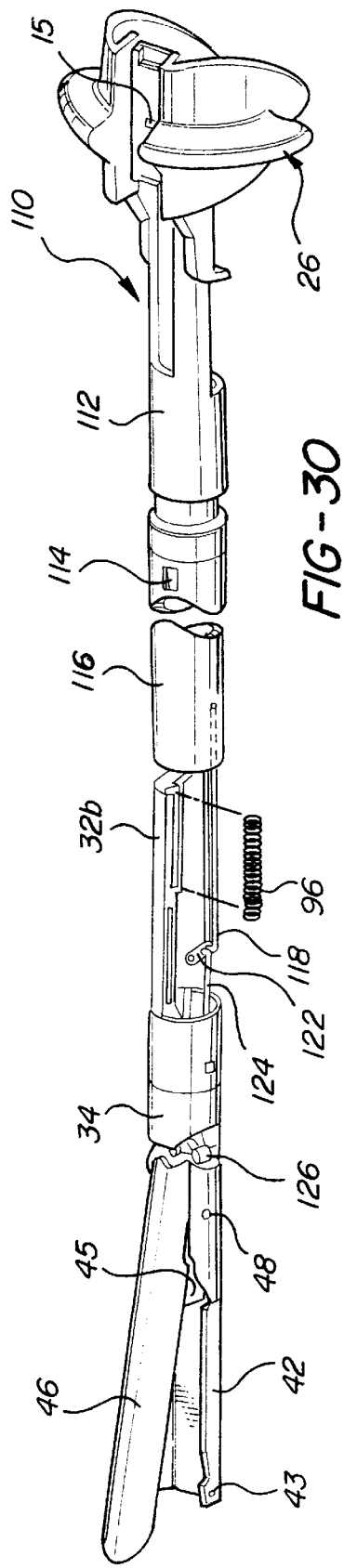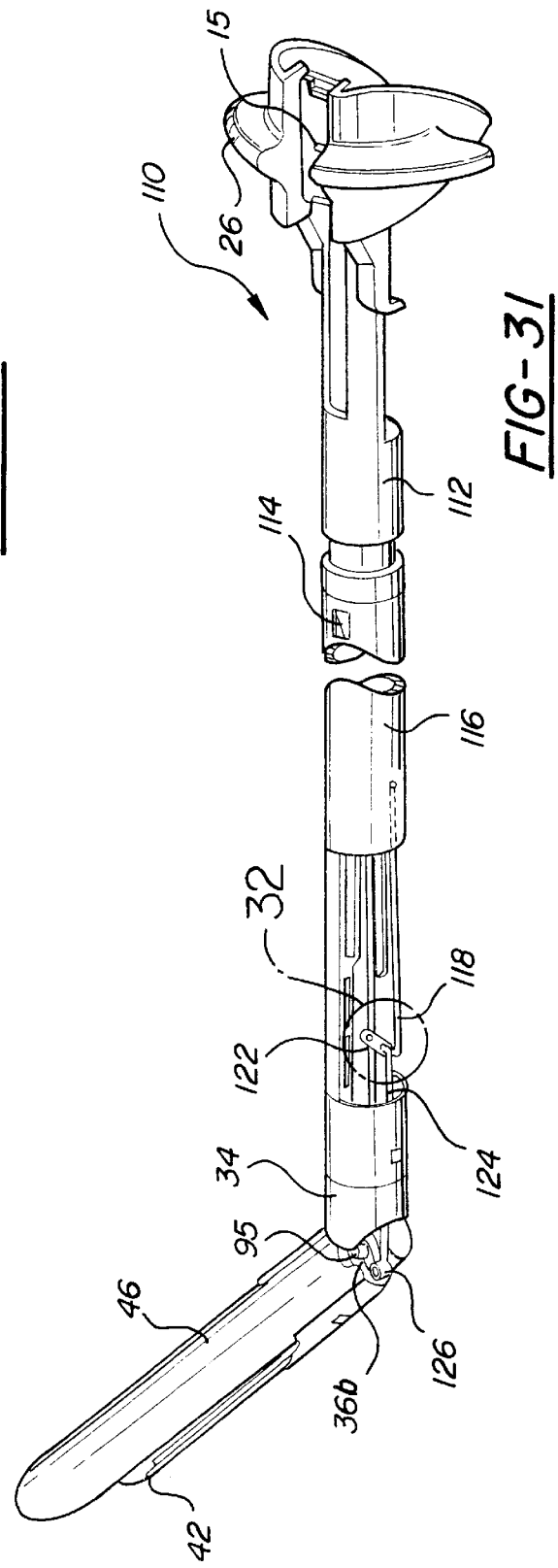

ARTICULATED SURGICAL INSTRUMENT WITH IMPROVED JAW CLOSURE MECHANISM

FIELD OF THE INVENTION

This invention relates generally to surgical instruments and, more particularly, to laparoscopic surgical instruments having an articulated operating tip and improved jaw closure mechanisms.

BACKGROUND OF THE INVENTION

Many traditional surgical procedures have required a surgeon to open up internal, operating sites by making relatively large incisions. More recently, however, surgeons are developing new techniques that enable many "open" surgical procedures to be performed laparoscopically. In laparoscopic procedures, a few relatively small incisions are made in the body cavity. Smaller incisions greatly reduce trauma to a patient and speed recovery.

Elongated cylindrical tubes, known in the art as cannulas, are placed in each incision. The design and use of cannulas is disclosed, for example, in applicant's co-pending U.S. patent application Ser. No. 08/189,318, which is hereby incorporated by reference. A laparoscopic, miniature video camera, or other viewing device is inserted through one of the cannulas so that the surgeon can see the operating site. Surgical instruments then are passed through the other cannulas to repair or remove tissue in the body cavity.

The typical configuration of such laparoscopic surgical instruments in certain respects is similar to surgical instruments designed for open surgery. The instrument generally includes a handle from which extends an elongated shaft. Controls are located on the handle so that a surgeon can manipulate and actuate the operating tip of the instrument.

Many types of laparoscopic surgical instruments have an operating tip which incorporates a pair of opposing, pivoting jaws. Examples of such instruments include laparoscopic scissors, graspers and linear staplers. The jaws pivot between open and closed positions, and the jaws are configured, as the case may be, to do the actual cutting, grasping, or stapling of tissue.

Designing a mechanism for controlling the operation of pivoting jaws in a laparoscopic instrument, however, presents a number of problems. For example, while space constraints are not a serious problem at the handle end of an instrument, a large part of the mechanical systems of a laparoscopic surgical instrument is located in the shaft and tip. Since those portions of the instrument must be small enough to fit through a relatively narrow cannula (generally having a diameter of 5 to 18 mm), space constraints in the shaft and at the tip can be quite severe.

Moreover, the shaft of laparoscopic instruments typically is not only narrower, but it also is longer than the shafts of instruments having the same general intended use in open surgery. The relatively long shaft enables a surgeon working outside a body cavity to manipulate organs and other tissue deep within the body. As the shafts of surgical instruments are lengthened and narrowed to adapt them to laparoscopic use, however, it becomes more difficult to design mechanisms which efficiently transfer forces from the handle-mounted controls to the operating tip of the instrument.

Finally, laparoscopic surgery inherently provides limited access to the interior of a patient's body cavity. The number of incisions preferably is kept to a minimum, and typically, no more than four cannulas are installed during a given surgical procedure. One of the cannulas is dedicated to a miniature video camera or other viewing device, and so a surgeon typically only has a few cannulas through which instruments may be inserted. Moreover, a cannula has restricted movement with respect to the body cavity, and angular movement of an instrument is constrained by the cannula. Surgeons, therefore, can find it difficult to reach all of the body tissue which must be operated on in a given procedure.

Designers have addressed this accessibility problem by providing instruments with a joint which allows the operating tip to articulate relative to the rest of the shaft. This allows the instrument to reach more areas in the body cavity with greater ease. Many conventional mechanisms for moving the pivoting jaws of laparoscopic instruments, however, cannot be used when the operating tip of the instrument is articulated.

For example, U.S. Pat. No. 5,170,925 to Madden et al. discloses two distinct types of jaw closure mechanisms. One type of mechanism includes a hollow tubular sheath or collar which slides over the jaws causing them to pivot closed. The other type of mechanism disclosed therein includes a driver which has a planar camming surface at its distal end which contacts and cams under a planar camming surface on the proximal end of the anvil, thereby causing the anvil to pivot closed. Neither of those jaw closure mechanisms, however, can accommodate articulation of the instrument tip.

Consequently different types of jaw closure mechanisms have been used in laparoscopic instruments which have pivoting jaws and an articulated operating tip. For example, U.S. Pat. No. 4,763,669 to J. Jaeger discloses a laparoscopic forceps-type instrument in which articulation and jaw closure is accomplished, inter alia, by a pair of pivoting links which can extend beyond the perimeter of the shaft. U.S. Pat. No. 5,312,023 to D. Green et al. discloses a laparoscopic linear stapler having an articulating and rotating tip. The jaw closure mechanism disclosed therein includes a cable loop which is pulled to generate pivoting force on a pulley mounted on a pivoting anvil. U.S. Pat. No. 5,330,502 to W. Hassler et al. discloses laparoscopic graspers and scissors with an articulating tip in which the jaws are closed by a pull cable. U.S. Pat. No. 5,423,471 to D. Mastri et al. shows a similar pull cable mechanism to close articulated jaws in an laparoscopic fastener applier. All of those instruments offer the significant advantage of having an articulating tip.

Designing a mechanism for controlling the operation of pivoting jaws in a laparoscopic instrument presents a number of different problems, but when the instrument has an articulated operating tip those problems are exacerbated and new problems are created. Articulating the operating tip of an instrument necessarily involves transmitting force through an articulation joint. Transmitting force through an articulation joint not only worsens the problem of efficient transfer of force through a relatively long, narrow shaft, but it also can generate forces which will stress the tip or cause it to move out of its desired position. Also, the instrument must incorporate a system to control articulation, and perhaps other mechanical systems, in an environment where space already is at a premium. Existing laparoscopic instruments with articulated, pivoting jaws have not satisfactorily addressed such problems.

It is, therefore, a general object of the invention to provide improved surgical instruments for use in laparoscopic procedures, such as laparoscopic linear staplers, graspers, scissors, and dissectors, having a pair of opposed jaws and an articulated operating tip. A more specific object is to provide such instruments with an improved system for moving the jaws between their open and closed positions.

Another object is to provide such instruments wherein the jaw closure system efficiently and reliably transfers force from the instrument's controls through the articulation joint to the jaws. A related object is to provide a jaw closure system which does not tend to move the articulated tip out of an articulated position when the jaws are closed. Another related object is to provide a jaw closure system in which the response of the jaws to actuation of controls is substantially the same regardless of the position in which the tip may be articulated.

A further object is to provide such instruments wherein the jaw closure system is of relatively simple design. A related object is to provide a jaw closure system which occupies relatively little space in the instrument and facilitates the incorporation of additional mechanical systems in the instrument.

Yet another object of the subject invention is to provide laparoscopic surgical instruments having a pair of opposed jaws and an articulated operating tip wherein all of the above mentioned advantages are realized.

Those and other objects and advantages of the invention will be apparent to those skilled in the art upon reading the following detailed description and upon reference to the drawings.

SUMMARY OF THE INVENTION

This invention provides an articulated surgical instrument for use in laparoscopic surgical procedures including, in general, a handle, an elongated shaft, and a tip. The shaft is coupled to the handle, and the tip is pivotally coupled to the distal end of the shaft for articulation about an articulation axis.

The tip includes two opposed jaws. The jaws are pivotally coupled at a pivot axis for movement between an open position and a closed position, and at least one of the jaws has a camming portion proximal to the pivot axis of the jaws.

The instrument further includes a camming driver disposed in the shaft for reciprocating movement between a proximal position and a distal position. The camming driver has a camming portion. The drive camming portion contacts the jaw camming portion at a cam point. Movement of the camming driver from its proximal position to its distal position causes the jaws to pivot from their open position to their closed positions.

Preferably, one of the camming portions defines a curved surface and the other camming portion defines a planar surface as such surfaces contact each other at a cam point. For example, the jaw camming portion preferably is a hemispherically-shaped projection and the driver camming portion is a ramp. Most preferably, the hemispherically-shaped projection is centered proximate to the articulation axis such that the cam point is proximate to the articulation axis as well.

In other aspects, the subject invention provides an articulated surgical instrument for use in laparoscopic surgical procedures wherein the tip is pivotally coupled to the shaft by an articulation joint which has a leaf spring which biases the jaws in an open position.

It will be appreciated, therefore, that the jaw closure mechanism of the novel instruments can accommodate articulation of the tip, yet still efficiently and reliably moves the jaws between their open and closed positions and utilizes a relatively simple and easily constructed design. Further, by selecting the shape and location of the camming portions as described herein, the force generated by the camming driver to close the jaws can be more closely transmitted at the articulation axis regardless of the degree of articulation. Thus, forces which might induce stress on the jaws or cause the tip to articulate out of its intended position are minimized.

BRIEF DESCRIPTION OF THE DRAWINGS

FIG. 6 is a top plan view of instrument 10;

FIG. 7 is a bottom plan view of instrument 10;

FIGS. 8A and 8B (collectively FIG. 8) constitute an exploded, left side perspective view of the handle assembly 20 and certain components of the shaft assembly 30 of instrument 10;

FIG. 9 is an exploded, left side perspective view of the tip assembly 40 of instrument 10;

FIG. 10 is a left side, bottom perspective view of the anvil 46 of instrument 10;

FIG. 11 is a top, left side perspective view of the cartridge assembly 50 of instrument 10;

FIG. 12 is a left side, bottom perspective view of the cartridge housing shroud 56 of instrument 10;

FIG. 17 is a rear, left side, top perspective view of selected components of the cartridge assembly 50 of instrument 10;

FIG. 18 is a side elevational view of the cartridge assembly 50 components shown in FIG. 17;

FIG. 27 is a partially exploded, top perspective view of the firing system 130 and selected other components of instrument 10;

FIG. 28 is a partially exploded, top perspective, partial view of selected components of the shaft 30 and tip 40 assemblies of instrument 10, showing in particular certain components supporting the drive cable 148 of the firing system 130;

FIG. 29 is a side elevational, partial view similar to FIG. 28 showing selected other components supporting the drive cable 148 of firing system 130;

FIG. 30 is a partially exploded, top, side perspective view of the articulation control system 110 and selected other components of instrument 10, showing the tip 40 in its unarticulated position;

FIG. 31 is a view similar to FIG. 30, showing the tip 40 in an articulated position;

DESCRIPTION OF THE PREFERRED EMBODIMENTS

A laparoscopic instrument 10 constructed in accordance with the teachings of the instant invention is shown generally in FIGS. 1–7. The illustrated embodiment 10 of the invention is configured as an articulated linear stapler which is capable of both stapling and cutting tissue. The instrument 10 is designed for use in bowel reconstructions and other surgical procedures where it is necessary to join and divide body tissue. Bowel reconstruction, for example, is a procedure in which diseased portions of the bowel are removed. The bowel is a tubular shaped organ through which body wastes are processed. It is necessary to close off portions of the bowel before tissue is cut so as to minimize bleeding and discharge of bowel contents into a patient's body cavity.

Consequently, the instrument 10 lays down opposing rows of staples to hemostatically close, for example, a portion of the bowel at two parallel seams. In the same operation, the instrument 10 then divides that portion of the bowel which is between the opposing stapled seams. Since that part of the bowel adjacent to the incision in large part has been closed by the rows of staples, discharge of bowel contents is minimized.

Those skilled in the art will readily appreciate, however, that the invention is not limited to the disclosed linear stapler 10 in particular or to linear staplers in general. On the contrary, the teachings of the instant invention can be employed in articulated laparoscopic instruments of widely varying designs, purposes, and uses without departing from the scope or the spirit of the invention. For example, graspers, scissors, and dissectors can be constructed in accordance with the subject invention. Linear staplers which do not simultaneously divide tissue may be constructed as well.

Figure 1:
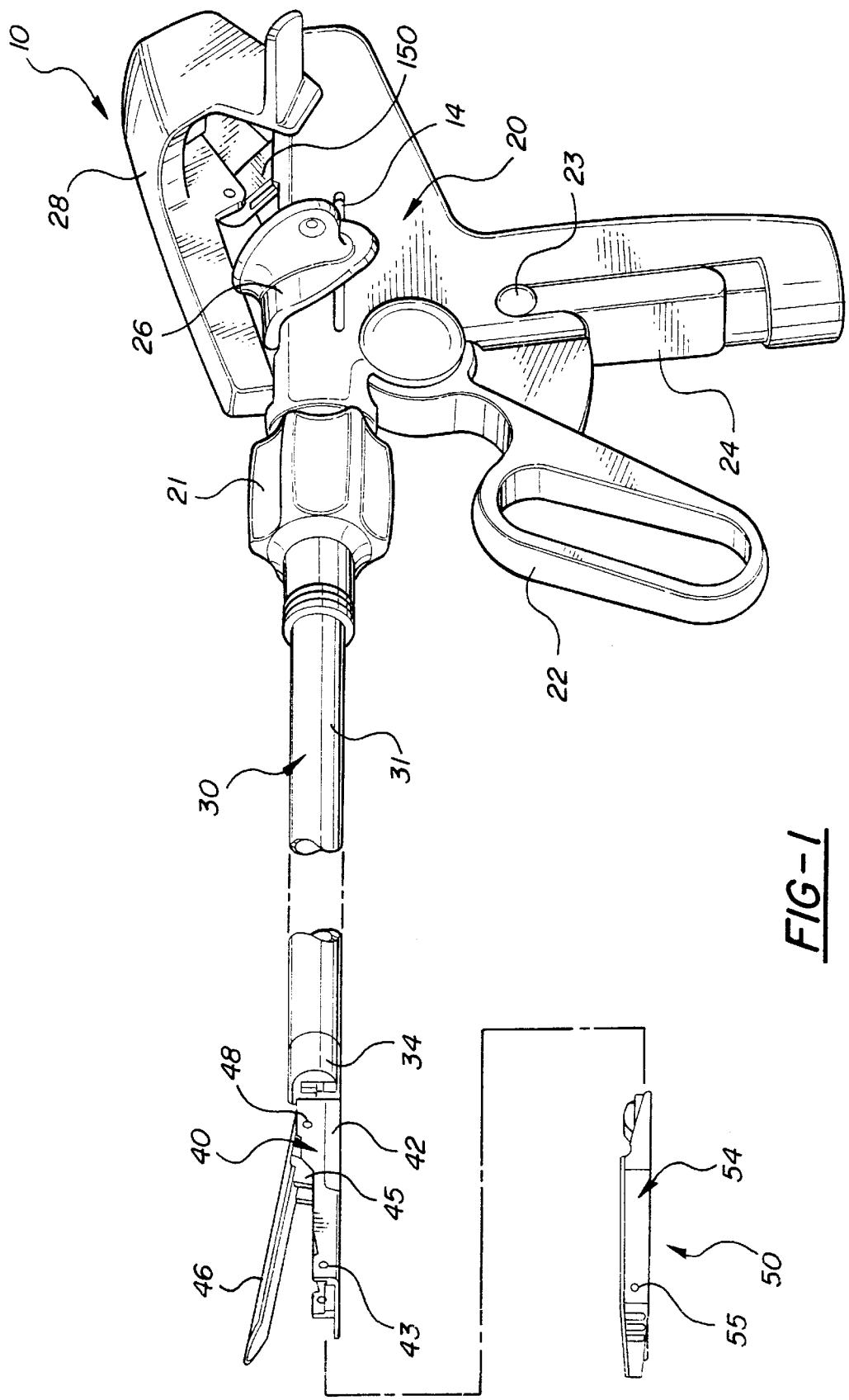
FIG. 1 is a front, left side and partially exploded perspective view of a preferred embodiment 10 of the subject invention, wherein instrument 10 is a laparoscopic linear stapler/divider with a rotating shaft and an articulating tip having replaceable staple cartridges.
Figure 2:
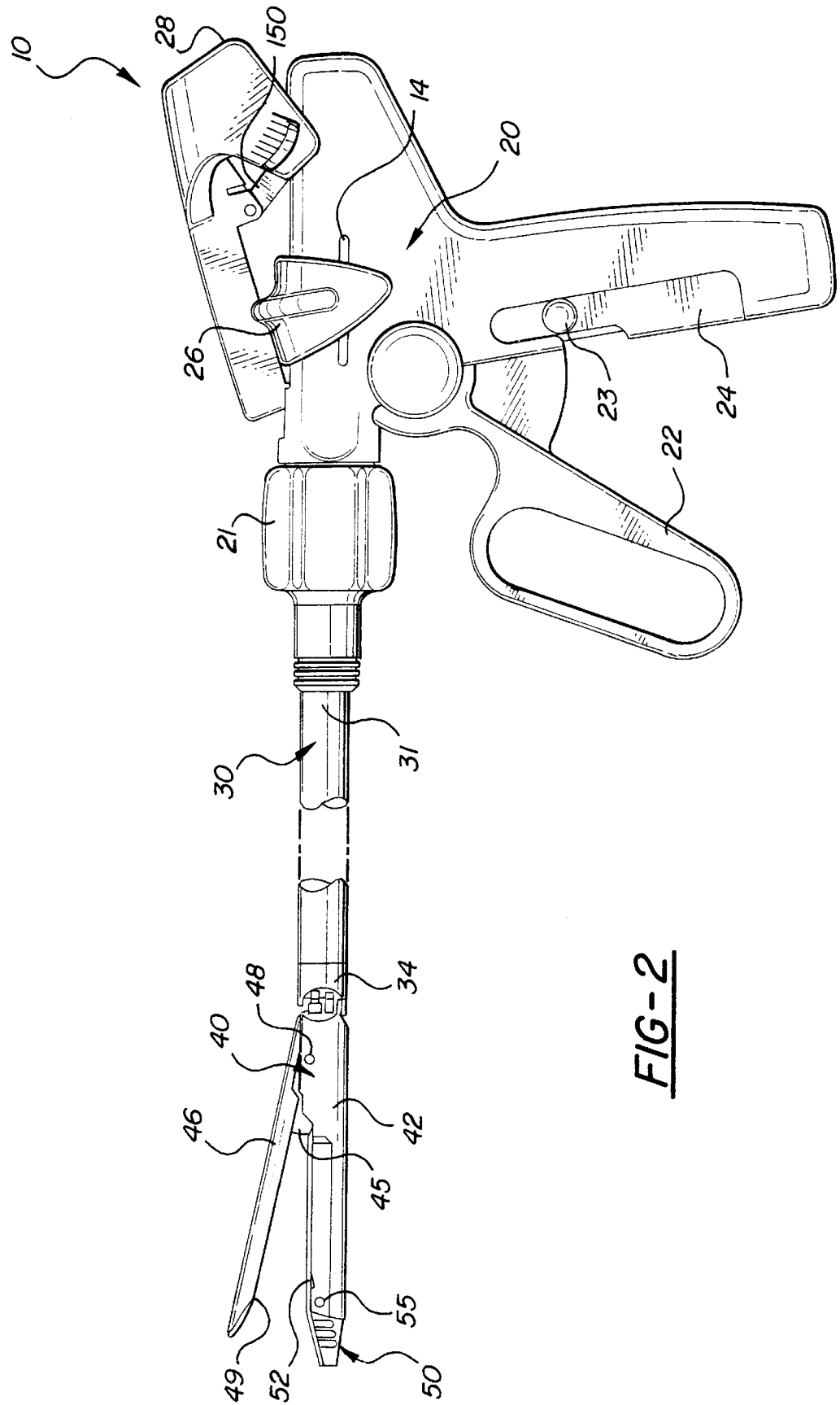
FIG. 2 is a left elevational view of instrument 10 showing the instrument 10 with its jaws in the open position.
Figure 3:
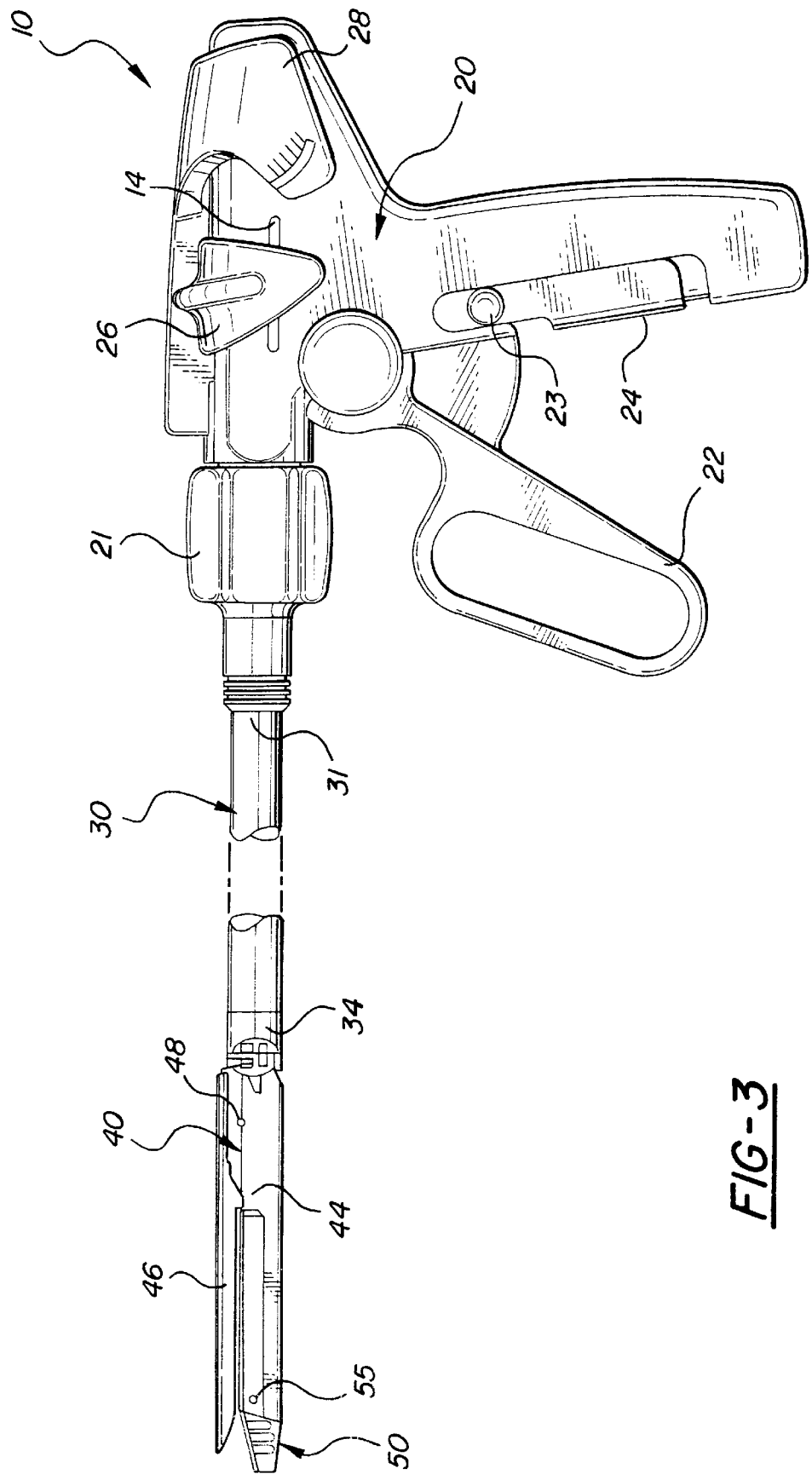
FIG. 3 is an elevational view similar to FIG. 2, but showing the instrument 10 with its jaws in the clamped or closed position.
Figures 4, 5:
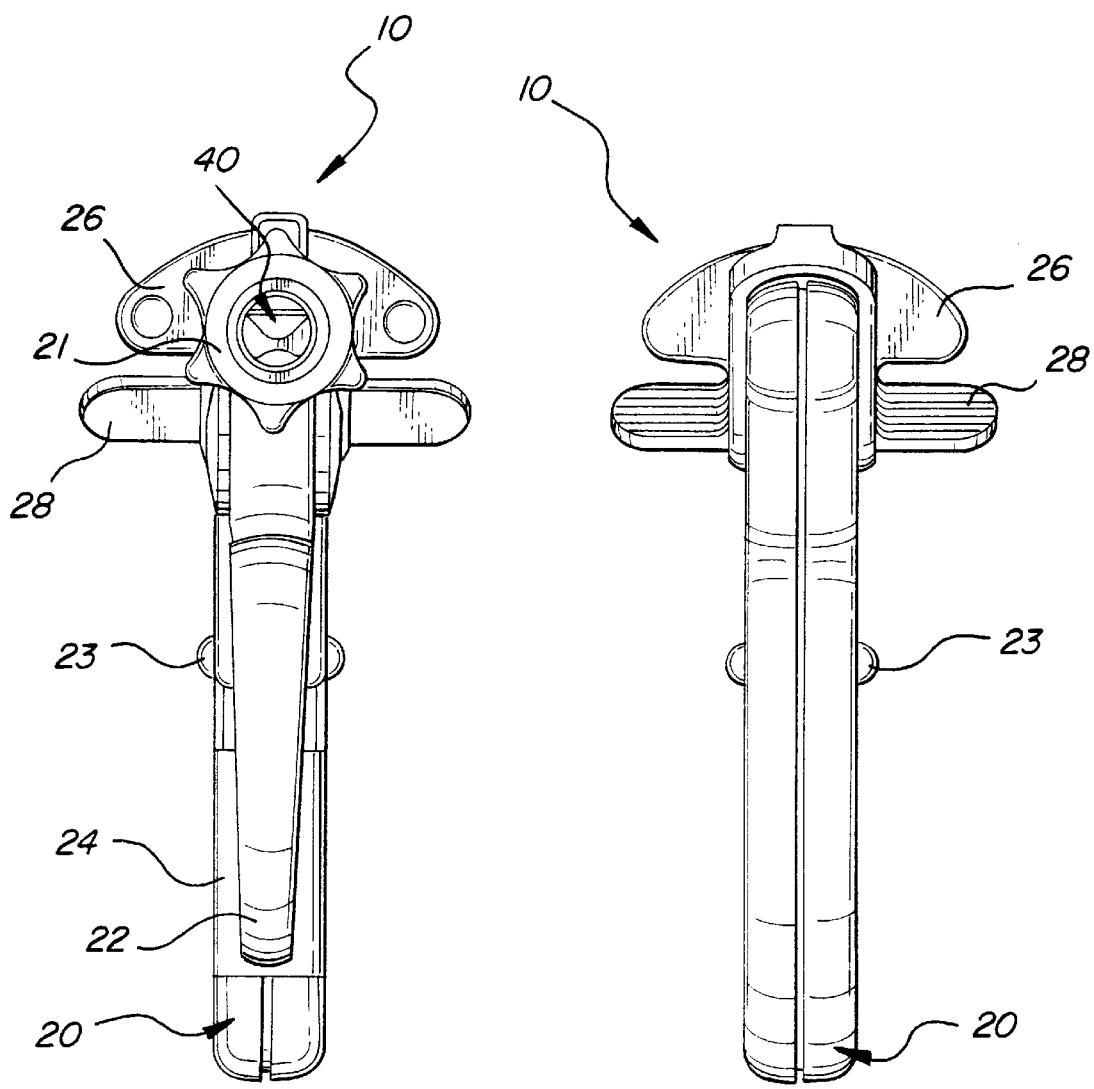
FIG. 4 is a front elevational view of instrument 10.
FIG. 5 is a rear elevational view of instrument 10.

The laparoscopic instrument 10, as best seen in FIGS. 1–3, generally includes a handle 20, an elongated shaft 30, and a tip 40. In general, the handle 20 allows a surgeon to comfortably grasp the instrument 10 and provides the surgeon with easy access to the controls or actuators which can be manipulated to operate the various mechanical systems incorporated into the instrument 10. For example, as shown in FIG. 2, the handle 20 includes the following actuators: a rotation knob 21 which a user can manipulate to rotate the shaft 30 about its longitudinal axis; a firing trigger 22 to actuate a firing system; a safety switch 24 to release a safety lockout system so the firing system can be actuated; an articulation slide 26 to actuate an articulation system; and a clamp-up lever 28 to actuate a jaw closure system.

The overall shape of the handle is determined in large part by the usual ergonomic considerations. Accordingly, the handle 20 in the illustrated embodiment is configured as a pistol-type grip which can be easily manipulated by a surgeon. Those skilled in the art will readily appreciate, however, that other handle designs are known and can be employed without departing from the scope or the spirit of the invention. Similarly, although the various actuators associated with the handle 20 have been illustrated, those skilled in the art will appreciate that other types of actuators with different ergonomic or operating characteristics could be substituted for the illustrated actuators without departing from the scope or the spirit of the invention. Once ergonomic and operating criteria are met, however, there remains considerable room to provide a variety of ornamental details which enhance the aesthetic appeal of the instrument.

Figure 8B:
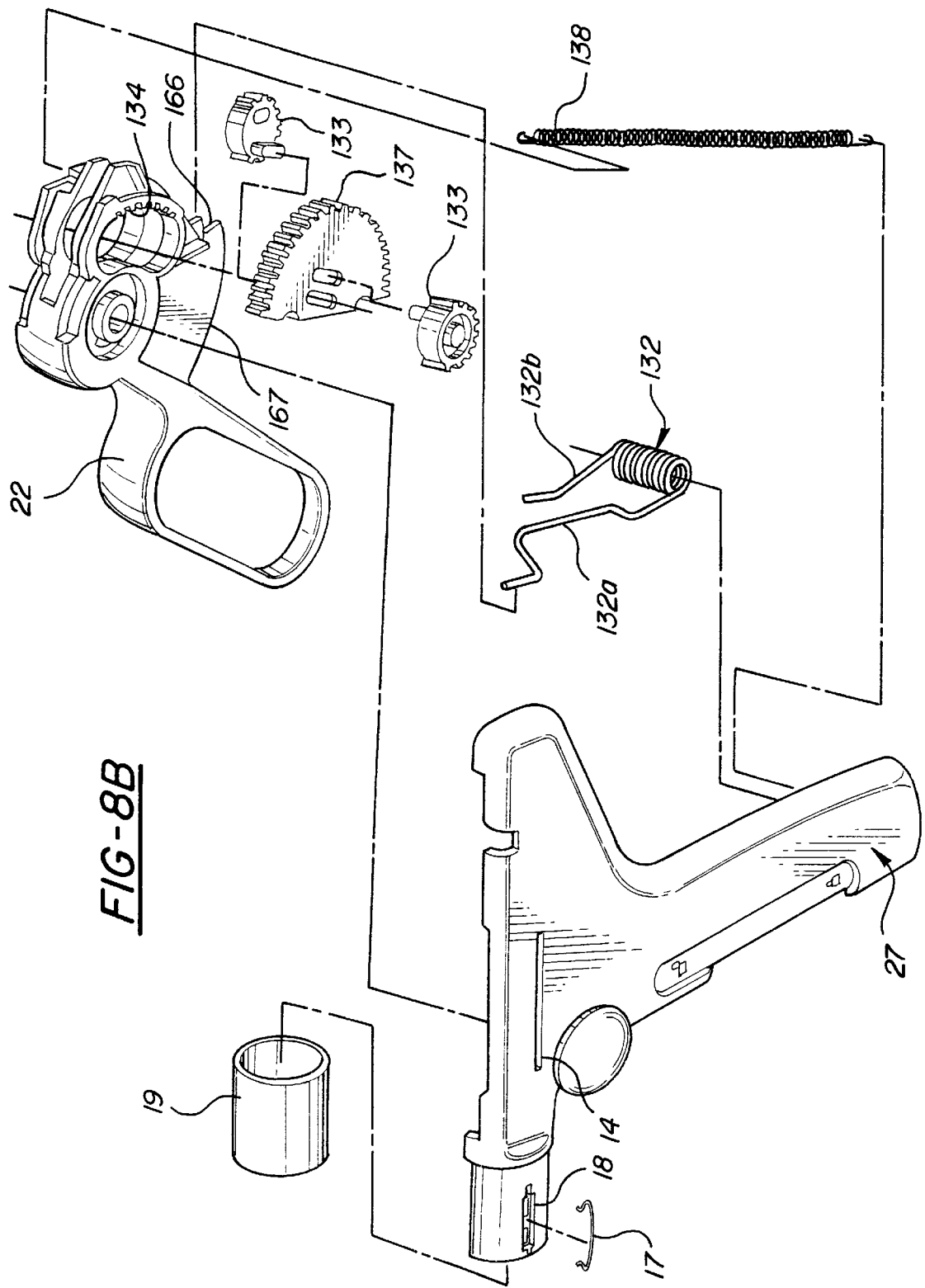

The handle 20 also houses and supports various components of the instrument's mechanical systems. To this end, the handle 20 preferably comprises two molded plastic halves 25, 27, as shown in FIG. 8, which include various projections, openings, and other design features that support and interact with the mechanical systems as further described below.

The elongated shaft 30, which includes a proximal end coupled to the handle 20 and a distal end coupled to the tip 40, performs several functions. First, like the handle 20, the shaft 30 provides a housing for various components of the mechanical systems of the instrument 10. Accordingly, the shaft assembly 30 includes an outer shaft tube 31 which is generally open at each end. The proximal end of shaft tube 31 is connected to the rotation knob 21 via connector 38 and washer 39, as can be appreciated from FIG. 8A, connector 38 having a pair of arms which snap into suitable openings in rotation knob 21. A clevis body 32 comprising clevis halves 32a and 32b shown in FIG. 27 is disposed in the shaft tube 31 near its distal end. An insert 33 in turn is disposed in the clevis body 32. An end piece 34 shown, e.g., in FIGS. 1 and 30 is mounted over the distal end of the shaft tube 31. The shaft tube 31, the clevis body 32, the clevis body insert 33, and the shaft end piece 34, as will be apparent from the discussion which follows, provide support for and/or accommodate various components of the instrument's mechanical systems.

The shaft 30 also extends the tip 40 a distance from the handle 20 sufficient to enable a surgeon working outside a patient's body to reach and manipulate tissue in the patient's body cavity. In order to permit the instrument 10 to be used through a trocar cannula or the like, the elongated shaft 30 preferably is substantially cylindrical. In the preferred embodiment, the shaft 30 is about 315 mm long. Preferably, the cross-section diameter of the shaft 30 is chosen to enable the instrument 10 to be used with commercially available cannulas. For example, many commercially available cannulas have nominal diameters of 5 mm, 6 mm, 8 mm, 10 mm, 10.5 mm, 12 mm, or 18 mm. The diameter of the shaft 30 preferably will be chosen with the dimensions of those commercially available cannulas in mind.

In order to provide greater accessibility to tissue in a body cavity and to enable a surgeon to comfortably manipulate that tissue, the shaft 30 preferably is rotatable relative to the handle 20. In order to facilitate this rotation, the shaft 30 is provided with the rotation knob 21, as shown in FIG. 1. Rotating knob 21 will rotate the shaft 30 by a like amount. The knob 21 is disposed at the distal end of the handle 20 so that it is easily accessible to a surgeon. As will be appreciated from FIG. 8B, the handle 20 includes a resilient member 17 which is held in cavity 18 on the distal end of handle half 27 by collar 19, such that the distal end of resilient member 17 mates with a plurality of notches (not shown) formed in the inner surface of the knob 21 to hold the shaft 30 in discrete positions relative to the handle 20 as it is rotated.

While rotation of the shaft relative to the handle is preferred, instruments constructed in accordance with the subject invention may incorporate fixed shafts. Similarly, the precise manner in which the shaft is rotatably coupled to the handle forms no part of the subject invention. The rotational coupling of the shaft and the various mechanisms passing through that coupling which are disclosed herein are believed to contribute to the efficient construction and operation of the instrument, but other such couplings are known and may be used.

The tip of the novel instruments comprise two opposed jaws which are pivotally coupled on a pivot axis for movement between an open position and a closed position. Accordingly, tip 40 of instrument 10 includes a receiver 42 and an anvil 46, as shown in FIG. 1. The receiver 42 is an elongated arm-like structure having a U-shaped cross-section, as better seen in FIG. 9, which is designed to slidably receive a removable staple cartridge assembly 50, as shown in FIG. 1. The anvil 46 also is an elongated arm-like structure. The anvil 46 has staple forming recesses 61 in its lower surface 49, as seen best in FIG. 10. As described in further detail below, the anvil 46 and receiver 42 are constructed, in cooperation with various other components of the instrument 10, to clamp over and then to staple and divide tissue.

It will be appreciated, however, that instruments of the subject invention may have jaws which are configured for different uses. For example, the jaws may be configured as cutting blades in a laparoscopic scissors or biopsy forceps or as grasping arms in laparoscopic graspers without departing from the scope or spirit of the invention. Thus, it will be understood that the term "jaws" is used in the context of the subject invention to include any pair of opposed members which pivot between an open position and closed position to perform an operation on body tissue.

The tip of the novel instruments is coupled to the distal end of the shaft for articulation relative to the shaft about an articulation axis. Consequently, a surgeon is able to reach more areas in a patient's body cavity more easily. In the preferred embodiment 10, for example, anvil 46 is provided with an articulation bore 47 as shown in FIG. 9. The shaft assembly 30 is provided with a like pair of articulation bores, specifically, a bore 37 in a leaf spring 36 extending through shaft end piece 34 and a bore 35 disposed on the opposite side of the distal end of shaft end piece 34, as shown in FIG. 29. As will be appreciated by comparing FIGS. 9 and 29, a pin 95 passes through bore 47 on anvil 46 and bore 37 in leaf spring 36. Similarly, a post 107 extends from receiver 42 and passes through bore 35 on shaft end piece 34. Thus, the tip 40 may articulate relative to the shaft 30 about an articulation axis passing generally through bores 47, 37, 35, pin 95, and post 107.

The articulating tip of the novel instruments, however, may be coupled to the shaft in different way, especially when different jaws, articulation control systems, or firing systems are utilized. For example, the jaws may be constructed such that only one jaw is directly coupled to the shaft.

In the preferred embodiment 10, tissue is secured between the lower surface 49 of the anvil 46 and an upper surface 52 of the cartridge 50 before the tissue is stapled and divided. To this end, the anvil 46 and the receiver 42 each include a pair of aligned bores 44 located near their proximal ends, as shown in FIG. 9. A pin 48 passes through the bores 44 of the anvil 46 and the receiver 42. Pin 48 secures the jaws 42, 46 together in such a manner that they may be moved between an open position shown in FIG. 2 and a closed position shown in FIG. 3.

More precisely, as jaws 42, 46 are closed, anvil 46 pivots relative to receiver 42 which remains substantially stationary This arrangement is preferred in the context of embodiment 10 and linear staplers in general, especially when such instruments are articulated. As will be appreciated from the discussion which follows, the staple cartridge assembly 50 and receiver 42 interact with other mechanical systems in the instrument, such as the articulation and firing systems. Those systems must be designed to accommodate articulation of the tip 40, including receiver 42, relative to the shaft 30. The design and operation of the instrument 10 is simplified, however, if movement of the receiver 42 is substantially limited to the plane of articulation.

It will be appreciated, however, that it is not essential that a particular one or the other of the jaws remain stationary, especially when graspers, scissors and the like are constructed in accordance with the subject invention. Such instruments have fewer mechanical systems. Other instrument's mechanical systems may accommodate pivoting of both jaw members. Accordingly, it will be understood that the subject invention encompasses instruments having pivoting jaws which move between open and closed positions regardless of whether a particular one or both of the jaws pivot relative to the other.

Figure 24:
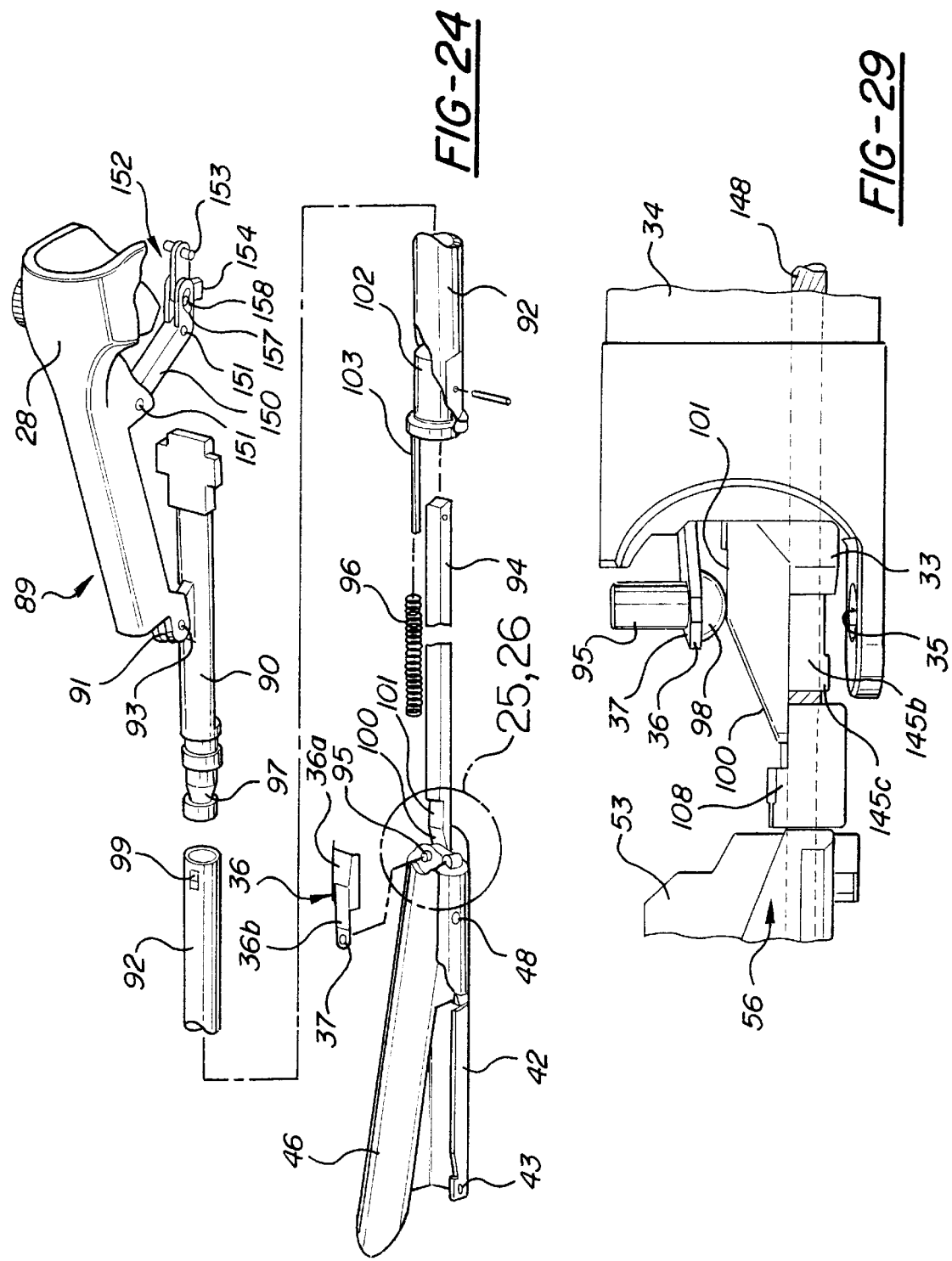
FIG. 24 is a partially exploded, top perspective view of the jaw closure system 89 and selected other components of instrument 10.
Figure 25:
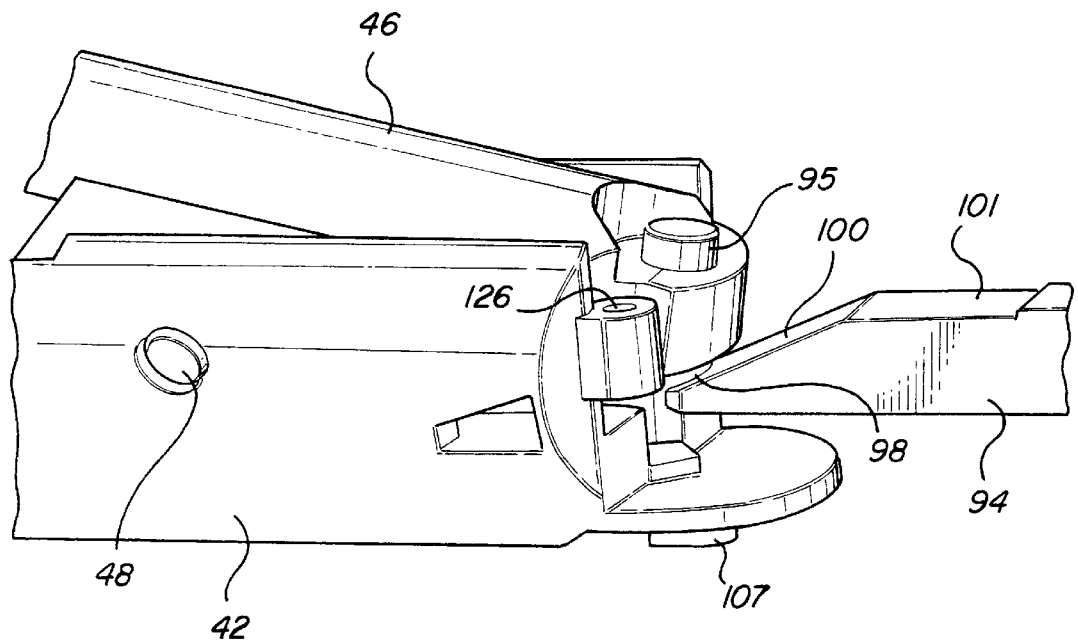
FIG. 25 is a top, left side perspective, partial view of the camming driver 94 and tip assembly 40 of instrument 10, showing camming driver 94 in the open jaw position.
Figure 26:
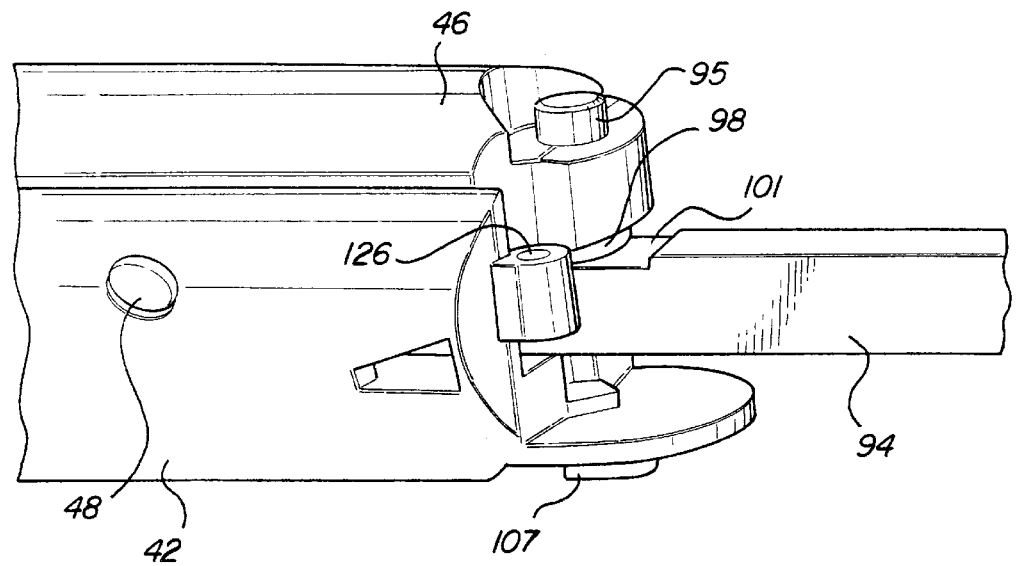
FIG. 26 is a view similar to FIG. 25 showing camming driver 94 in the closed jaw position.

In order to move the jaws 42, 46 between the open and closed positions, the instrument 10 is provided with a jaw closure system 89 as illustrated in FIGS. 24–26. More particularly, the jaw closure system 89 biases the anvil 46 in its open position and enables the anvil 46 to be moved into a closed position and held there. This jaw closure system 89 includes the clamp-up lever 28 mentioned above; a clamp-up driver 90; a clamp-up tube 92; a camming driver 94; a return spring 96; leaf spring 36 mentioned above, and a cam projection 98.

As illustrated in FIGS. 24 and 33–36, the clamp-up lever 28 is pivotally coupled to the clamp-up driver 90 via a pin 93 which extends through bores in a pair of arms 91 extending from its distal end. The proximal end of the clamp-up lever 28 is secured to the handle 20 via link 150. Link 150 is pivotally coupled to both the clamp-up lever 28 and to the handle 20 by pins 151. The clamp-up driver 90 is disposed in the handle 20 for reciprocating longitudinal movement between a proximal position and a distal position. As a result, when the clamp-up lever 28 is moved from the raised, open position illustrated in FIG. 2 to the lowered, closed position illustrated in FIG. 3, the clamp-up driver 90 is driven from its proximal position to its distal position. In other words, this arrangement translates the downward pivoting motion of the lever 28 into distal movement of the driver 90, as may be appreciated by comparing FIGS. 34 and 35.

As best appreciated from FIGS. 24 and 33–36, the distal end of the driver 90 is rotatably coupled to the proximal end of the clamp-up tube 92. More specifically, driver 90 is an elongated, substantially cylindrically-shaped tube which includes an annular trough 97 disposed about the outer circumference of its distal end. Likewise, clamp-up tube 92 is an elongated, substantially cylindrically-shaped tube. The clamp-up tube 92 is disposed in the shaft 30 for reciprocating, longitudinal movement between a proximal position and a distal position. The proximal end of the clamp-up tube 92 includes a pair of opposed tabs 99. Tabs 99 angle slightly inward such that they snap into and mate with the trough 97 on the driver 90 to secure the clamp-up tube 92 and the driver 90 together while permitting relative rotation between these two components. This arrangement permits the driver 90 to transfer longitudinal motion to the clamp-up tube 92, and vice versa, while simultaneously permitting relative rotation between the components of the jaw closure system 89 disposed in the shaft 30 and the components disposed in the handle 20. Thus, the jaw closure system 89 is adapted to accommodate rotation of the shaft 30 relative to the handle 20.

The clamp-up driver 90 and clamp-up tube 92 preferably are elongated, substantially cylindrically-shaped tubes as shown. When configured in such a manner, as will become apparent from the description of the articulation control and firing systems which follows, they may accommodate and be accommodated within tubular components of other mechanical systems in the instrument 10. Further, since the shaft tube 31 is an elongated, substantially cylindrically-shaped tube, by configuring the driver 90 and tube 92 in a like manner space within the shaft tube 31 is more efficiently utilized. Moreover, since their essential function is that of a reciprocating drive shaft, by situating them more or less concentrically to the longitudinal axis of the shaft 30, they transmit force with less of a moment which otherwise might tend to bend the shaft 30.

Laparoscopic instruments of the subject invention may be configured to accomplish a variety of procedures, and frequently the instruments incorporate a number of complex mechanical systems which must be designed, each with a view toward the other. Consequently, the precise configuration of the clamp-up lever 28, the clamp-up driver 90, and the clamp-up tube 92 and the manner in which they are interconnected is subject to wide variation as will be appreciated by those working in the art.

The novel instruments also comprise a camming driver which is disposed in the shaft for reciprocating movement between a proximal position and a distal position. Accordingly, as shown in FIG. 27, camming driver 94 is an elongated rod having a substantially rectangular cross section. Camming driver 94 is disposed in the elongated insert 33 carried in clevis 32 disposed at the distal end of shaft assembly 30. More particularly, camming driver 94 can slide within a closely-fitting, U-shaped channel extending the length of clevis body insert 33.

As shown in FIG. 24, the clamp-up tube 92 is coupled to the camming driver 94 via a plug 102. The longitudinal movements of the tube 92, therefore, are transmitted to the camming driver 94 through this direct connection.

In order to control the movements of the camming driver 94, the return spring 96 is positioned, preferably in a preloaded state, around pin 103 on the plug 102 which extends into a receiving pocket in the clevis body 32 (see FIG. 30). Distal movements of the clamp-up tube 92 compress spring 96 between the plug 102 and the clevis body 32. Accordingly, spring 96 biases camming driver 94 towards its proximal position and the clamp-up lever 28 toward its open position. The return spring 96 also will assist the camming driver 94, the clamp-up tube 92, the clamp-up driver 90, and the clamp-up lever 28 in their return movements when the jaws 42, 46 are to be released from the clamped position.

Thus, lever 28, clamp-up driver 90, clamp-up tube 92, and return spring 96 cooperate to control the movement of the camming driver 94 between its proximal and distal positions. Other mechanisms for generating and controlling such movement, however, may be used and, indeed, may be desirable depending on the other features and mechanical systems of a particular instrument. For example, if the shaft was fixed relative to the handle the camming driver could be coupled directly to the lever or another actuator A variety of springs also may be utilized to bias the camming driver in its proximal position, and they may act directly on the camming driver or on other components of the mechanism.

As will be appreciated by comparing FIGS. 6, 24, 27, and 31, leaf spring 36 has a fixed end 36a which is mounted at the distal end of shaft assembly 30 between the distal end of clevis body 32 and the shaft end piece 34. Leaf spring has a free end 36b which extends distally though the shaft end piece 34. As previously noted, anvil 46 is coupled to leaf spring 36 via bore 37 in spring free end 36b to permit articulation of tip 40 relative to shaft 30. The free end 36b of leaf spring 36, however, is coupled to the anvil 46 proximal to the jaw pivot pin 48 on an upper surface of anvil 46 and, preferably, is preloaded against the anvil 46. Thus, leaf spring 36 also serves to bias anvil 46 in its open position.

It will be appreciated, therefore, that a leaf spring serves, in a simple and efficient manner, the dual purpose of coupling the tip for articulation and biasing the jaws in an open position. By incorporating a leaf spring into the articulation joint the design of the instrument is greatly simplified and other mechanical systems may be incorporated into the instrument more easily. Thus, the illustrated articulation joint is especially preferred, and the incorporation of a leaf spring into a articulation joint is itself another aspect of the subject invention.

At the same time, however, it will be appreciated that this aspect of the invention is subject to modification, especially when the jaws have different configurations. For example, the leaf spring may be mounted by any suitable means, and its fixed end may be mounted on the tip instead of on the shaft. Similarly, the leaf spring may bear against the lower surface of the anvil instead of against the upper surface Such modifications allow the leaf spring to serve its dual functions, and other equivalent modifications will be apparent to workers in the art.

In other aspects, however, the subject invention is not limited to the use of a leaf spring, and depending on the configuration of the jaws, other types of springs or resilient bodies may be used to bias the jaws in the open position. Likewise, in accordance with other aspects of the subject invention, the leaf spring need not be pivotally coupled to the tip, and may simply be used to bias the jaws while other types of articulation joints are used.

In accordance with the subject invention, at least one of the jaws has a camming portion which is situated proximal to the pivot axis of the jaws. The camming driver also is provided with a camming portion. As the camming driver moves from its proximal position to its distal position, the camming portion of the camming driver contacts the camming portion of the jaws at a camming point to pivot the jaws from their open position to their closed position.

In the preferred embodiment 10, for example, as most easily seen in the magnified views depicted in FIGS. 25 and 26, the distal end of the camming driver 94 forms a camming surface 100. Pin 95, which as noted above couples anvil 46 to leaf spring 36, also provides anvil 46 with a camming projection 98 on the underside of anvil 46 proximal to jaw pivot pin 48. The camming surface 100 of camming driver 94 and the camming projection 98 interact to pivot the anvil 46 relative to the receiver 42 and thereby to close the jaws 42, 46.

More specifically, when the camming driver 94 is driven distally from its proximal position by the pivoting of the lever 28 from the open to the closed positions and the subsequent distal movements of the driver 90 and the clamp-up tube 92, the camming surface 100 rides under the cam projection 98 as will be seen by comparing FIGS. 25 and 26. This movement of the camming driver 94 effectively lifts both the cam projection 98 and the proximal end of the anvil 46. Since cam projection 98 is situated proximal to jaw pivot pin 48, lifting of the cam projection 98 causes anvil 46 to pivot downward about pin 48 toward its closed position. When the jaws 42, 46 are positioned around body tissue, the pivoting of the anvil 46 firmly clamps the tissue between the surface 49 of anvil 46 and the upper surface 52 of the cartridge assembly 50 carried by the receiver 42.

Further in accordance with the subject invention, the camming portions of the jaw and camming driver are adapted such that they contact each other at a camming point. For example, the cam projection 98 on anvil 46 is a hemispherically-shaped projection and camming surface 100 on camming driver 94 is a planar ramped surface. Consequently, the hemispherical cam projection 98 and the planar ramped surface 100 define a mechanical point at which the contact and camming occurs. Because there is such a camming point, tip 40 may be articulated relative to the shaft 30 and to the camming driver 94. It is not necessary that the camming point be a point in the mathematical sense, but it will be appreciated that as the size of the camming contact area increases, articulation of the tip 40 will generate increasing torque in the jaws 42, 46 which will tend to cause them to twist out of the intended plane of articulation. Resistance to articulation likewise will be increased, and eventually, this torque will preclude any articulation of the jaws.

Preferably, the shape of the jaw and driver camming portions are coordinated to minimize any change in location or "travel" of the camming point as tip is articulated or the jaws are pivoted. Accordingly, the center of hemispherically-shaped projection 98 (i.e., the center of the imaginary sphere corresponding thereto) is located proximate to the articulation axis of the instrument 10. More specifically, as best appreciated by viewing anvil 46 in its closed position shown in FIGS. 26 and 29, the center of projection 98 is located on the axis which extends through bores 47, 37, 35, pin 95, and post 107. Consequently, when tip 40 is articulated, cam projection 98 will rotate, but it will not translate relative to camming surface 100. Further, the curved surface of projection 98 has an axis of symmetry which is proximate to the articulation axis. This ensures that movement of the anvil 46 in response to movement of the camming driver 94 is the same regardless of the angle to which the tip 40 is articulated.

It will be appreciated, however, that the center of cam projection 98 need not be situated exactly on the articulation axis. Indeed, because anvil 46 pivots on pin 48 relative to receiver 42 and because cam projection 98 is somewhat distant from the pin 48, the center of cam projection 98 moves proximally a short distance as anvil 46 pivots from its open to its closed position and there is some longitudinal travel of the camming point. Nevertheless, on average the center of cam projection 98 is sufficiently close to the articulation axis to ensure that the responsiveness of the anvil 46 does not change significantly as the tip 40 is articulated. As the center of the projection 98 becomes more remote from the axis, however, the response of the anvil 46 to movement of the camming driver 94 will become more variable and articulation of the tip 40 may cause the anvil 46 to move. On the other hand, travel of the camming point which results from movement of the projection 98 as anvil 46 pivots may be minimized somewhat by providing cam projection 98 with a prolate hemispheroid shape.

It also will be appreciated that by situating the center of hemispherically-shaped cam projection 98 on the articulation axis the cam point between cam projection 98 and camming surface 100 will be proximate to the articulation axis. Consequently, there is no need to transfer the clamping force of the camming driver "around a corner" when the tip is in an articulated position. The cam point need not be situated exactly on the articulation axis, but it will be appreciated that as it becomes more remote therefrom distal movement of the camming driver 94 when tip 40 is articulated will tend to cause further articulation of the tip 40 beyond its intended position. The camming driver 94 also will tend to cause twisting of the anvil 46 relative to the plane of articulation, and this torque can create some resistance to closing of the anvil 46.

Consequently, the hemispherically-shaped cam projection 98 and the planar ramped camming surface 100 provide efficient and predictable closure of the jaws 42, 46 regardless of the degree to which the tip 40 is articulated. The mechanical efficiency of that operation obviously can be varied or staged by changing the slope of camming surface 100.

It will be appreciated, however, that the precise shape of cam projection 98 and camming surface 100 may be varied without departing from the scope of the invention. Those camming portions may have different shapes so long as they contact each other at a camming point. For example, the camming projection may define other truncated spherical surfaces or other curved surfaces. Likewise, a planar camming surface could be provided on the pivoting jaw and a curved camming surface provided on the camming driver, or both the pivoting jaw and the camming driver could have a curved camming surfaces. If both jaws were designed to pivot, they each could be provided with a camming portion and the driving wedge then would have two camming portions. For example, each jaw could be provided with a hemispherically-shaped cam projection and the tip of the camming driver could be provided with an upper and lower ramped camming surface. The cam projection also need not be a separate piece; it may be an integral part of a jaw.

In instrument 10, it will be appreciated that relatively high clamping forces are transmitted through the cam point. Accordingly, camming driver 94 and pin 95 preferably are fabricated from relatively hard, durable materials such as steel. Moreover, the clamping forces, especially when the jaws 42, 46 are being clamped over relatively thick tissue, can generate considerable friction. One or both of the camming driver 94 and pin 95, or their respective camming surfaces 100, 98, therefore, may be provided with surface coatings designed to reduce the friction therebetween. Sintered PTFE coatings and the like, for example, may be provided. Alternately, silicone, PTFE, and similar lubricants may be used. Obviously, when lower clamping forces are expected, the need for such coatings and lubricants is less, and less durable materials may be used in fabricating the camming driver and pin.

In order to insure that jaws 42, 46 remain in the clamped or closed position despite the counteracting forces generated by the anvil leaf spring 36, the return spring 96, and any elasticity in the tissue clamped between the jaws 42, 46, the ramped surface 100 of the camming driver 94 terminates in a flat surface 101, as shown in FIGS. 25 and 26. Thus, after cam projection 98 has traversed the length of camming surface 100 it will come to rest on flat 101. The intersection between camming surface 100 and flat 101 may be radiussed slightly to allow easier movement of cam projection 98 over the intersection, especially when the jaws 42, 46 are being clamped over relatively thick tissue.

At this point, leaf spring 36 and the elasticity of clamped tissue generate sufficient friction between the cam projection 98 and flat 101 to counteract the force generated by spring 96. Consistent with that purpose, flat 101 is sufficiently parallel to the reciprocating movement of camming driver 94 so that cam projection 98 will remain thereon. At the same time, however, flat 101 may be angled slightly downward toward the distal end of the camming driver 94 so that the camming driver 94 may be moved off flat 101 more easily when the jaws 42, 46 are unclamped. It is believed an angle on the order of 5° will suffice for such purposes.

Alternately, flat 101 may be provided with a slight recess in which cam projection 98 may rest once the jaws 42, 46 are fully clamped. Such a recess will tend to hold the jaws 42, 46 more securely in their clamped position. The configuration of the recess and its angle relative to the camming driver 94 also may be adjusted to facilitate unclamping of the jaws 42, 46.

Thus, under normal circumstances, once the jaws 42, 46 are clamped over tissue the cam projection 98 will remain on flat 101, and camming driver 94 will remain in its distal, clamped position, until the camming driver 94 is manually moved proximally by lifting the clamp-up lever 28 from its lowered, clamped position. As a result, once the jaws 42, 46 are moved to the clamped position illustrated in FIG. 26, they will preferably remain in such position until a surgeon desires to open the jaws 42, 46.

The ability to hold the jaws in their closed position is highly preferable in linear staplers. Likewise, it may be a useful feature in laparoscopic graspers. It may or may not be desirable, however, in laparoscopic scissors, and thus it is not an essential aspect of the subject invention.

It will be appreciated from the foregoing description of the jaw closure system that it provides efficient and reliable jaw closure while still accommodating articulation of the tip. Importantly, however, it does so while utilizing a relatively simple design with a minimum number of parts. This simplicity of design facilitates assembly of the instrument, and it allows other mechanical systems to be incorporated into the instrument more easily.

Figure 32:
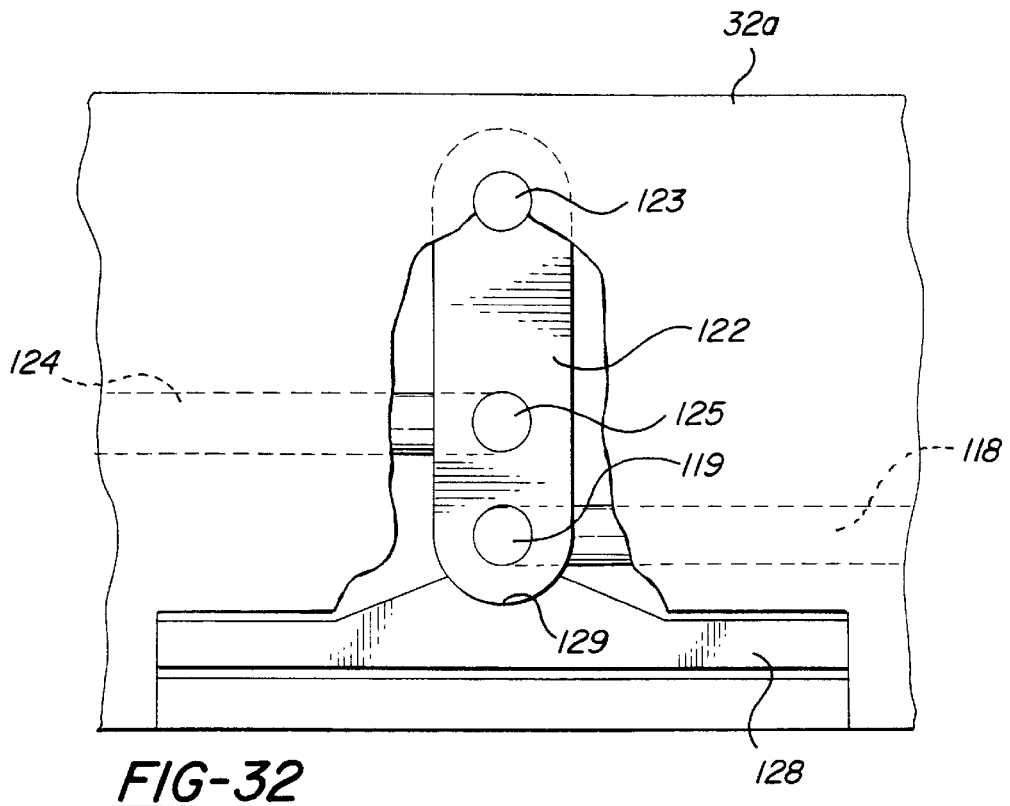
FIG. 32 is a left side elevational, partial view of shaft clevis half 32a, a portion thereof being torn away to show certain components of the articulation control system 110.

In order to provide control over the articulation of the tip 40, the instrument 10 is provided with an articulation control system 110 as illustrated in FIGS. 30–32. The articulation control system 110 includes the articulation slide control 26 mentioned above; an articulation driver 112; an articulation tube 116; a proximal rod 118; a desensitizing link 122; and a distal rod 124.

As discussed above, the articulation slide control 26 is associated with the handle 20 and can be manipulated by a surgeon to articulate the tip 40 to a desired position. To this end, and referring to FIG. 8, the articulation slide control 26 includes oppositely disposed, inwardly projecting longitudinal ribs 13 which engage longitudinal grooves 14 defined in the exterior surface of handle halves 25, 27. Thus, the slide control 26 is adapted for reciprocating longitudinal movement between a distal position and a proximal position.

Figure 22:
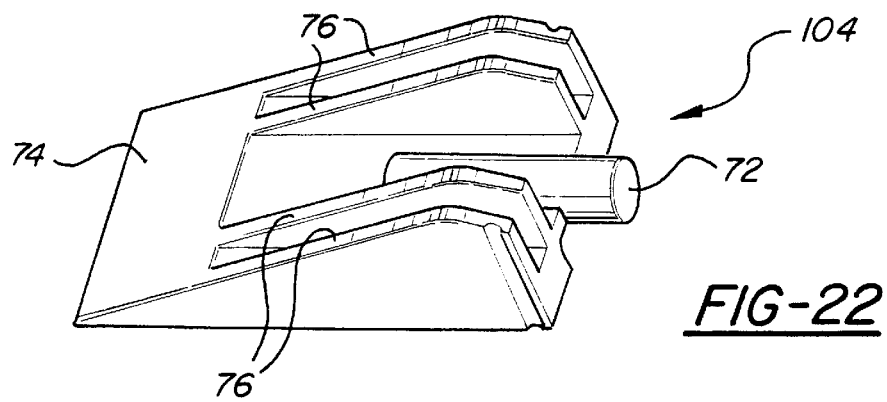
FIG. 22 is a similar perspective view of a first alternate sled 104 suitable for use in the staple cartridge 50 of instrument 10.

Moving the slide control 26 forward will cause the tip 40 to articulate to the right as illustrated in FIG. 31. Moving the slide control 26 rearward will cause the tip 40 to articulate to the left (not shown). (Of course, if the shaft 30 is rotated 180° from the position illustrated in FIGS. 22 and 23 such that the receiver 42 is disposed above the anvil 46, these directions will be reversed so that forward movement of the slide control 26 will pivot the tip 40 to the left and vice versa).

As shown in FIGS. 30 and 31, the distal end of the shaft 30 assembly is beveled on opposing sides to permit the jaws to articulate a full 45° in either direction. By providing the instrument 10 with the ability to articulate a full 45° in either direction from the aligned, neutral position, a surgeon can manipulate the instrument to reach more tissue areas more easily. Greater or lesser ranges of articulation may be provided, however. Likewise, the tip may be designed to articulate in a single direction if desired.

As illustrated in FIGS. 30 and 31, the articulation slide control 26 is directly connected to the articulation driver 112. Thus, movements of the slide control 26 are directly reflected in corresponding movements of the driver 112.

As in the jaw closure system 89 described above, the articulation control system 110 is adapted to accommodate rotation of the shaft 30 relative to the handle 20. To this end, the distal end of the articulation driver 112 is rotatably coupled to the proximal end of the articulation tube 116, as can be seen in FIGS. 30 and 33–36. As in the jaw closure system 89, this rotatable engagement is implemented by providing an annular trough 113 in the outer surface of the substantially cylindrical distal end of the articulation driver 112 and a pair of opposed tabs 114 formed in the proximal end of the articulation tube 116. The trough 113 and tabs 114 secure the articulation tube 116 and the driver 112 together while permitting relative rotation between these two components. This arrangement permits the driver 112 to transfer the longitudinal motion of the articulation control 26 to the articulation tube 116 while simultaneously permitting relative rotation between the portions of the articulation control system 110 disposed in the shaft 30 and the portions disposed in the handle 20.

The articulation tube 116 is coupled to the proximal rod 118 as shown in FIGS. 30 and 31. Thus, longitudinal movements of the articulation tube 116 cause corresponding movements in the proximal rod 118. These same movements are transferred to the distal rod 124. However, in order to attenuate the movement of the distal rod 124 relative to the movement of the proximal rod 118, and ultimately to attenuate the articulation of tip 40 relative to the sliding of control 26, the two rods 118, 124 are coupled through the desensitization link 122.

More particularly, as shown in FIGS. 30–31, proximal rod 118 is an elongated, relatively narrow, cylindrically-shaped rod extending generally through the shaft assembly 30 near its distal end. The proximal end of proximal rod 118 is pivotally coupled to the articulation tube 116. Thus, reciprocating longitudinal movements of the articulation tube 116 cause corresponding movements in the proximal rod 118.

Desensitizing link 122 of the preferred embodiment 10 is pivotally coupled to the clevis half 32a mounted near the distal end of shaft assembly 30. More precisely, as shown in FIG. 32, desensitizing link 122 is pivotally attached to clevis half 32a at pivot point 123 such that it can rotate about pivot point 123 in both directions. The distal end of proximal rod 118 is pivotally coupled to the desensitizing link 122 at pivot point 119. Accordingly, proximal rod 118 causes desensitizing link 122 to rotate as it reciprocates between its proximal and distal positions.

Distal rod 124, which is configured similarly to proximal rod 118, extends generally through the shaft assembly 30 at its distal end. The proximal end of distal rod 124 is pivotally coupled to the desensitizing link 122 at pivot point 125. Rotation of the desensitizing link 122, therefore, causes distal rod 124 to reciprocate longitudinally within the shaft 30.

Figure 23:
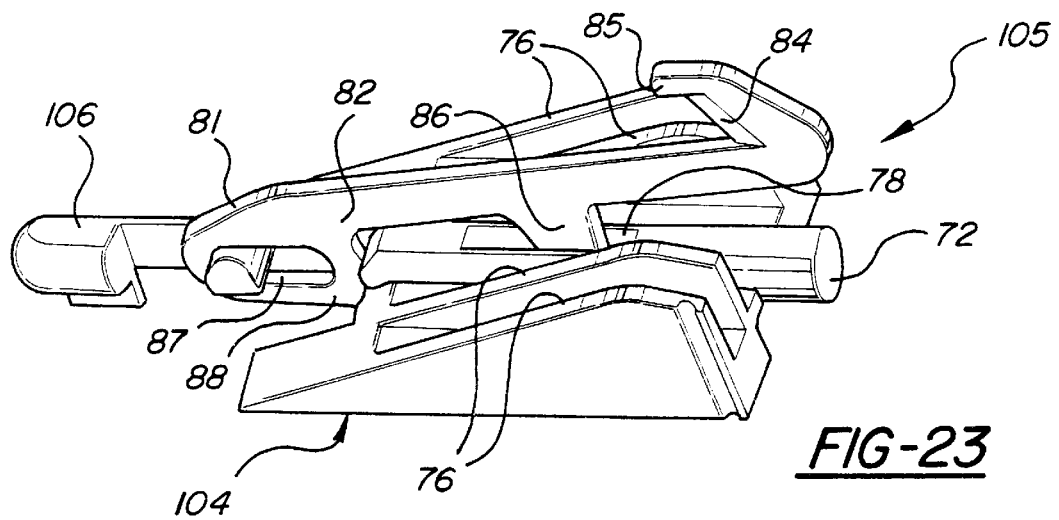
FIG. 23 is a similar perspective view of second alternate sled 105 suitable for use in the staple cartridge 50 of instrument 10.

Distal rod 124 is coupled at its distal end to a bore 126 positioned near the proximal end of the receiver 42. As shown in FIGS. 30 and 31, the bore 126 is positioned near the left side of the receiver 42. As a result, distal movements of the distal rod 124 will apply a pushing force to the left side of the receiver 42 thereby causing the tip 40 to articulate or pivot to the right (to an observer looking down the shaft 30 when the receiver 42 is positioned beneath the anvil 46 as shown in FIG. 23). Conversely, proximal movements of the distal rod 124 will apply an off center pulling force to the receiver 42 thereby causing the tip 40 to articulate in the opposite direction.

Desensitization link 122, as best seen in FIG. 32, is an elongated arm-like structure. The pivot 123 connection to clevis half 32a is at one end of the link 122 and the pivot 119 connection to the proximal rod 118 is at the other end of link 122. The pivot 125 connection to the distal rod 124 is in the middle of link 122. More to the point, the distance between the distal rod pivot point 125 and the link pivot point 123 is less than the distance between the proximal rod pivot point 119 and the link pivot point 123. Movement of the distal rod 124, therefore, will be attenuated relative to movement of proximal rod 118. Moreover, because movement of the distal rod 124 is attenuated by desensitization link 122, articulation of the tip 40 relative to movement of slide 26 will be attenuated as well.

The system for firing the instrument 10 will be described in further detail below, but suffice it to say at this point that the firing system creates some increasing resistance to the articulation of tip 40 as the degree of articulation increases. Although this resistance to articulation is relatively low, a surgeon generally will prefer a uniform feel to an instrument. The fact that articulation of the instrument is met with increasing resistance could be discomforting. Accordingly, the articulation control system preferably is designed to offset this effect.

In the preferred embodiment 10, for example, pivot point 123 is fixed proximate to an imaginary line (not shown) extending between the point where proximal rod 118 connects to articulation tube 116 and the point where distal rod 124 connects to receiver 42. Consequently, when desensitizing link 122 is in its neutral, "unarticulated" position (shown in FIG. 30), it bends proximal rod 118 and distal rod 124 out of the positions they normally would occupy. As rods 118, 124 are moved distally or proximally to articulate the tip 40 (shown in FIG. 31), therefore, the stress in rods 118, 124 is relieved, and rods 118, 124 urge the tip 40 towards an articulated position. The articulating force thus generated tends to offset the increasing resistance of the tip 40 to articulation which is caused by flexing of the firing system.

The firing system of an articulated instrument, since it necessarily must transfer force around a corner, also can create a moment which may cause the tip to straighten or otherwise move when the instrument is fired in an articulated position. The firing system 130 of the illustrated instrument 10, as discussed further below, is designed to minimize such moments and any resulting movement. Preferably, however, the articulation control system also is designed to minimize movement of the tip when the instrument is fired in an articulated position.

For example, as shown in FIG. 8A, the slide control 26 of the instrument 10 has a tooth 15 upstanding from an upper surface thereof. The clamp-up lever 28 has an elastic body 16 which is composed of a natural or synthetic rubber or another elastomeric material. The elastic body 16 is disposed in a cavity provided on the undersurface of the clamp-up lever 28 for such purposes. As best appreciated from FIGS. 33–36, when the clamp-up lever 28 is closed, the tooth 15 bites into the elastic body 16, thereby immobilizing the articulation slide control 26. Consequently, the tip 40 cannot be articulated when the jaws 42, 46 are closed, but more importantly, the tip 40 is stabilized and resistant to any firing forces which otherwise would tend to cause the tip 40 to move.

Since the instrument 10 cannot be inserted through a cannula when it is articulated, the articulation control system preferably is designed so that the tip 40 may be located easily and reliably in the unarticulated position. For example, as will be appreciated from FIG. 32, clevis half 32a, to which desensitization link 122 is mounted, has an integral leaf spring portion 128 which extends under desensitization link 122. Leaf spring 128 has a shouldered detent 129 into and out of which the end of desensitization link 122 may pivot. Flexing of leaf spring 128 allows desensitization link 122 to pivot into and out of engagement with detent 129 more easily. Thus, the interaction between the detent 129 and the end of desensitization link 122 provides a surgeon with tactile feedback concerning the position of the tip 40 and also helps prevent the tip 40 from being inadvertently moved from its centered position relative to the shaft 30 during use and handling.

The illustrated articulation control system 110 is preferred because it allows the surgeon to reliably, efficiently, and easily control articulation of the operating tip of the instrument. The advantages and features of the illustrated articulation control system are described in further detail in an application of Jeffrey R. Oberlein and Mark A. Penrod, entitled Articulated Surgical Instrument With Improved Articulation Control Mechanism and filed concurrently herewith. The disclosure of that application is hereby incorporated by reference. It will be appreciated, however, that the manner in which articulation of the operating tip is controlled is not part of the subject invention.

The illustrated linear stapler 10 is designed to form two parallel, hemostatic stapled seams and to divide the tissue between the seams in a single operation. Accordingly, cartridge assembly 50 includes a housing 54, a plurality of staples 60, a plurality of staple drivers 64, 66, and a movable sled 70 having a cutting knife 80 as illustrated in FIGS. 9–21. As will be explained in further detail below, the moveable sled 70 sequentially actuates the staple drivers 64, 66 which in turn drive staples 60 out of the cartridge, through the tissue, and against the anvil 46. The knife 80 moves with the sled 70 to divide the tissue shortly after the stapled seams are formed.

Housing 54 comprises two components, namely, a shroud 56 and a base 58 which collectively define a central cavity and various other openings, tracks, and supports designed to accommodate the other components of the cartridge assembly 50. The shroud 56 has the upper surface 52 referred to above. The upper surface 52 extends between the proximal and distal ends of the shroud 56 parallel to the longitudinal axis of the shroud 56, as can be seen in FIG. 9. The upper surface of base 58 provides a floor 68 which extends generally parallel to and below the upper surface 52 of shroud 56. The base 58 and shroud 56 define a central cavity through which, as described in further detail below, sled 70 may travel.

As shown in FIG. 9, the housing shroud 56 defines a plurality of staple openings 51. Each of the staple openings 51 frictionally holds a staple 60 such that the tips of the staples 60 are disposed near the upper surface 52 of the shroud 56. The staple openings 51 provide passageways for upward movement of staples 60 from the cartridge assembly 50 into tissue clamped against the upper surface 52 of the shroud 56.

The staple openings 51 are arranged in two spaced sets such that staples 60 ejected therefrom will form two parallel stapled seams. Each set includes three parallel rows of staple openings 51. Two of the rows, one in each set, are staggered with respect to the other four rows to facilitate the formation of hemostatic seams.

Figure 13:
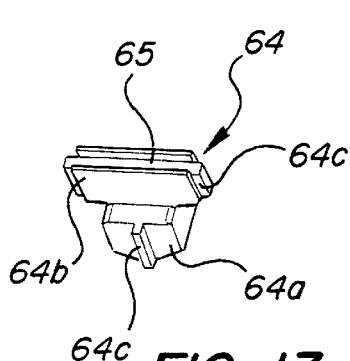
FIG. 13 is a top, side perspective view of a single staple driver 64 of instrument 10.
Figure 14:
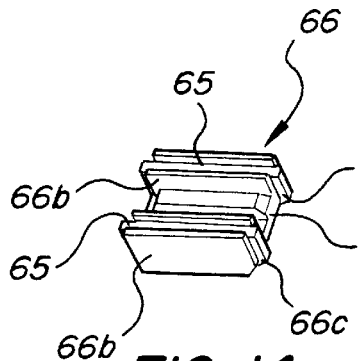
FIG. 14 is a top, right side perspective view of a double staple driver 66 of instrument 10.
Figure 15:
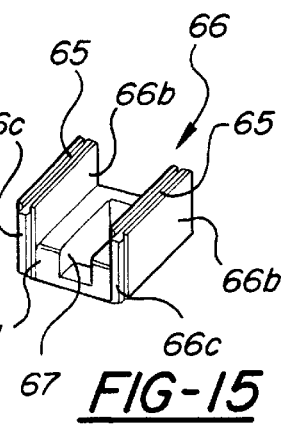
FIG. 15 is left side, front, top perspective view of the double staple driver 66 shown in FIG. 14.

A staple driver 64, 66 is associated with each staple 60 and staple opening 51, as best appreciated by comparing FIGS. 9, 12 and 17–18. The plurality of drivers 64, 66 include two types of drivers, namely, single staple drivers 64 and double staple drivers 66 as shown in FIGS. 13–15. As their names suggest, the single staple drivers 64 are designed to drive one staple 60 and the double staple drivers 66 are designed to simultaneously drive two staples 60. As illustrated in FIG. 13, the single staple driving members 64 include a base 64a supporting an integral plate 64b extending upwards from and across the base 64a on or about its lateral midpoint. The bottom of the base 64a provides a camming surface which, as described in further detail below, interacts with the sled 70. The upper surface of plate 64b defines a U-shaped staple trough 65 which receives and supports an inverted staple 60 as shown in FIGS. 17–18. In contrast, as shown in FIGS. 14–15, the double staple drivers 66 include a base 66a with two integral plates 66b extending upwards from the edges of base 66a. The bottom of base 66a provides a camming surface, and the upper surface of each plate 66b defines a staple trough 65.

The staple drivers 64, 66 are arranged in two parallel rows, one row on either side of the longitudinal center plane of the housing 54, as can be seen in FIGS. 17–18. Each row of staple drivers 64, 66 includes alternating single drivers 64 and double drivers 66 arranged such that the plates 64b of the single drivers 64 extend upwards in a staggered fashion between the plates 66b of the double drivers 66. The bases 64a, 66a of the staple drivers 64, 66 are arranged end to end such that the lower camming surfaces thereof are aligned.

As will be more fully appreciated from the description which follows, each row of staple drivers is associated with one of the stapled seams which are formed by instrument 10. The single staple drivers 64 in each row drive the staples 60 in the offset, middle row of each set of staple openings 51. The double staple drivers 66 drive the staples 60 in the outer rows of each set of staple openings 51.

Figure 16:
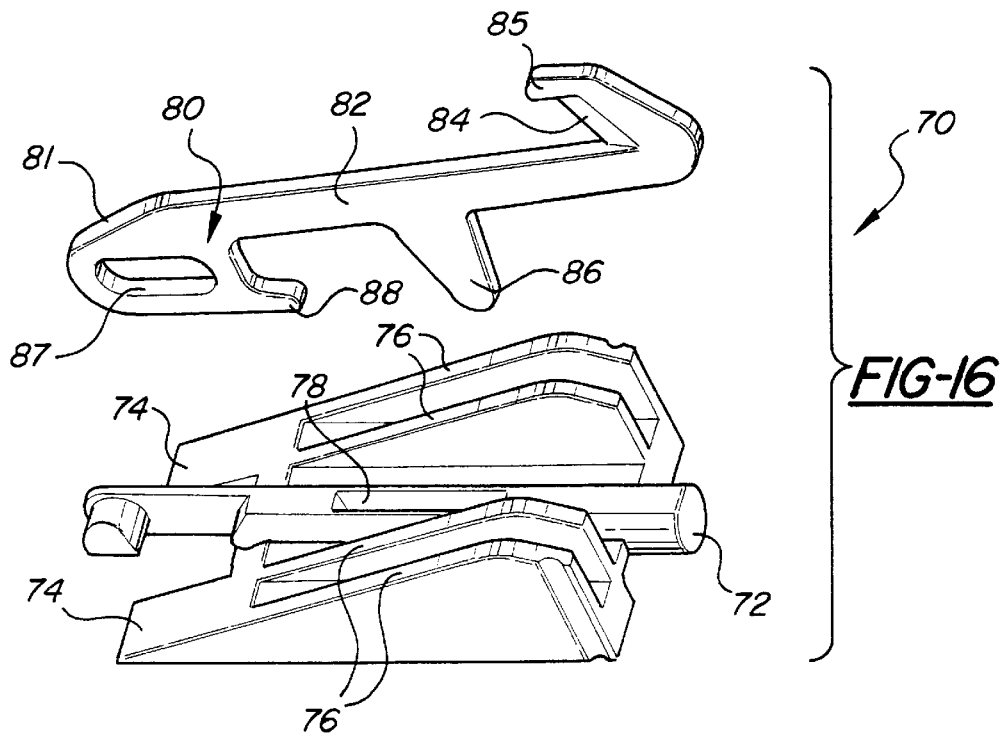
FIG. 16 is an exploded, top, left side perspective view of the staple cartridge sled 70 of instrument 10 including a knife 80.

The cartridge assembly 50 also includes the moveable sled 70 mentioned above. Sled 70 is adapted to actuate the staple drivers as it travels distally through the cartridge assembly 50. Accordingly, as best shown in FIG. 16, the preferred embodiment of sled 70 generally has a wedge-shaped body. More particularly, the sled 70 has two relatively wide, leading ramped upper surfaces 74. Each leading ramped surface 74 leads into two, relatively widely spaced, narrower trailing ramped surfaces 76. The ramped surfaces 74, 76 sequentially cam under staple drivers 64, 66 thereby translating the distal motion of the sled 70 to upward motion of the staple drivers 64, 66.

More particularly, when the cartridge 50 in its initial, "loaded" state, sled 70 is situated generally at the proximal end of cartridge 50. Staple drivers 64, 66 are adjacent the floor 68 of housing 54, and staples 60 are disposed within the staple openings 51. As the instrument is fired, the sled is driven distally by a firing system which is described in further detail below.

As best appreciated from FIGS. 17–18, when the sled 70 travels distally through the cartridge 50, the leading ramped surfaces 74 contact the bases 66a of the most proximal double staple drivers 66 in each set of staple drivers 64, 66. The sled 70 continues forward and begins camming those most proximal double staple drivers 66 upward, and the double staple drivers 66 in turn begin driving their associated staples out of the staple openings 51 toward the anvil 46. The proximal side of the bases 66a of double staple drivers 66 are ramped at an angle complementary to the ramped upper surfaces 74, 76 of sled 70 to facilitate this camming action.

The staple drivers 64, 66 in each row are arranged in an end-to-end fashion such that the base 66a of a double staple driver 66 is overlapped by the plates 64b of single staple drivers 64 adjacent to the double staple driver 66. In order to ensure that the double staple drivers 66 are not hindered in their upward movement by this overlap, and that they move independently of single staple drivers 64, the bases 66a of the double staple drivers 66 each are provided with a recess 67 in the distal side of their upper surface, as seen best in FIG. 15. Recesses 67 provide clearance between the base 66a of a double staple driver 66 and the overlapping plate 64b of the single staple driver 64 distal thereto. In other words, as a double staple driver 64 moves upwards, the recess 67 accommodates the overlapping portion of the plate 64b of the as yet undisplaced single staple driver 64 which is located distally thereto, thereby ensuring that the double staple driver 66 does not engage and displace the single staple driver 64 as it is cammed upwards by the sled 70.

As the sled 70 continues through the housing 54 in the distal direction it then contacts the most proximal single staple drivers 64 in each row of staple drivers 64, 66 and begins camming them upward. The proximal side of bases 64a of single staple drivers 64 also are ramped in a manner similar to the bases 66a of double staple drivers 66 to facilitate this upward camming. The sled 70 continues traveling distally, thereby sequentially camming a pair of double staple drivers 66 (one in each row of staple drivers 64, 66), a pair of single staple drivers 64, and so on until, by the time the sled 70 has reached its distal most position all staple drivers have been driven completely upward such that the plates 64b, 66b extend into the staple openings 51 and have fully ejected all staples 60.

The shroud 56 and base 58 collectively define openings and tracks for the respective movement of the sled 70 and staple drivers 64, 66. More particularly, the shroud 56 includes a plurality of columns 57 as shown in FIG. 12. Columns 57 extend generally downward from shroud 56 adjacent to staple openings 51 and are arranged in six parallel rows. The two outer rows of columns 57a, 57f are disposed adjacent the walls of the housing 54. The four inner rows of columns 57a, 57c, 57d, 57e are disposed between the outer walls.

The columns 57 have different lengths depending upon their location within the housing 54. Specifically, the columns 57a, 57f located in the outer rows adjacent the walls of the shroud 56 extend from the top of the shroud 56 to the floor 68 whereas the columns 57b, 57c, 57d, 57e in the four inner rows terminate before reaching the floor 68. Thus, an opening or distance which extends substantially the length of the cartridge is formed between the bottom of the columns 57b, 57c, 57d, 57e in the inner rows and the floor 68. It will be appreciated that this opening accommodates passage of the lower portion of sled 70 as it moves distally through the cartridge.

Columns 57 also are adapted to provide tracks for the staple drivers 64, 66 as they are cammed upward by sled 70. Accordingly, columns 57 are provided with channels in their proximal and distal ends which mate with projections 64c, 66c on each end of the plates 64b, 66b of the staple drivers 64, 66 as may be seen by comparing FIGS. 12–15. Likewise, the sides of columns 57a, 57c, 57d, 57f are provided with channels which mate with similar projections 64c on the ends of base 64a of the single staple drivers 64. The bases 66b of double staple drivers 66 have a passageway (not shown) through which columns 57b, 57e extend. The interaction of the drivers 64, 66 and their projections 64c, 66c with the columns 57 and their channels serve to maintain the alignment of the drivers 64, 66 as they drive their associated staples 60 out of the cartridge assembly 50.

In order to insure the staples 60 driven out of the cartridge assembly 50 are properly formed, the anvil 46 which clamps tissue against the upper surface 52 of the shroud 56 is provided with staple forming recesses 61 having inwardly sloped surfaces as shown in FIG. 10. When the anvil 46 is pivoted to the clamped position, recesses 61 are aligned with the staple openings 51. As a result, when staples 60 are driven through and out of the staple openings 51 by the staple drivers 64, 66, they pass through the clamped tissue until they impinge upon the recesses 61 on the anvil 46. The inwardly sloped surfaces of the recesses 61 cause the staple legs to bend towards one another to thereby grip the tissue in a manner known in the art.

The housing 54 is dimensioned to removably engage the receiver 42 of the tip 40. To this end, as can be seen in FIG. 9, the distal portion of the housing 54 is provided with two oppositely disposed posts 55 which engage bores or openings 43 in the distal end of the receiver 42 when the cartridge assembly 50 is inserted into the receiver 42. In addition, the anvil 46 is provided with four tissue stop ears 45. As their name implies, tissue stop ears 45 prevent tissue from extending too far into the jaws 42, 46 (i.e., past the most proximal staple openings 51) thereby ensuring that all of the tissue clamped by the jaws 42, 46 is stapled. When the anvil 46 is in the closed position, however, the inner two ears 45 mate with receptacles 63a formed in the upper surface 52 of the shroud 56, and the outer two ears 45 mate with recesses 63b on the sides of shroud 56. The interaction of the ears 45 and the receptacles 63 lock the cartridge assembly 50 in place during firing of the instrument. Finally, the proximal portion of the housing 54 is positioned beneath the pin 48 when the cartridge assembly 50 is disposed in the receiver 42 to further secure the cartridge 50 during use and handling. The engagement of the posts 55 and openings 43, the engagement of the ears 45 and receptacles 63, and the engagement of the housing 54 and the pin 48 can be overcome by opening the jaws 42, 46 and pulling the cartridge assembly 50 distally. Thus, the instrument may be fired repeatedly by replacement of spent cartridges with new ones.

Figure 19:
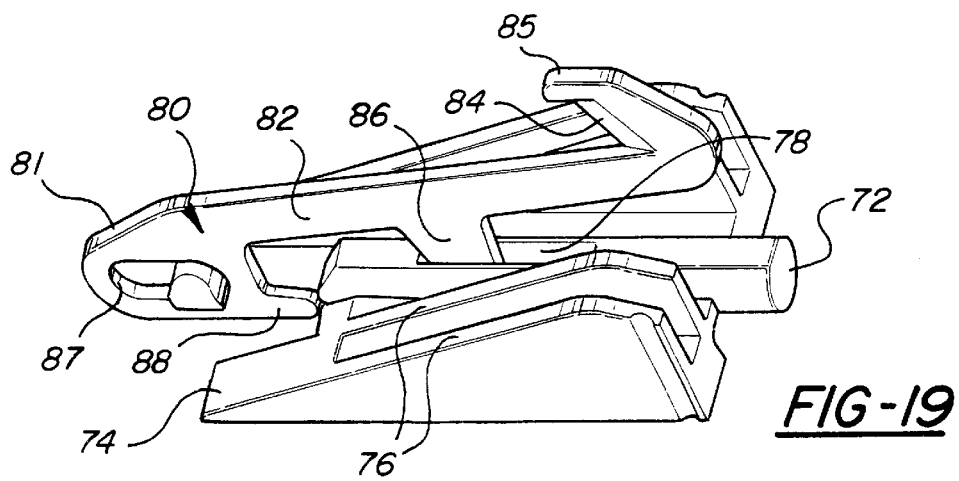
FIGS. 19–21 are rear, left side, top perspective views of the sled 70 shown in FIG. 16, showing in particular the sled knife 80 in its various positions.
Figure 20:
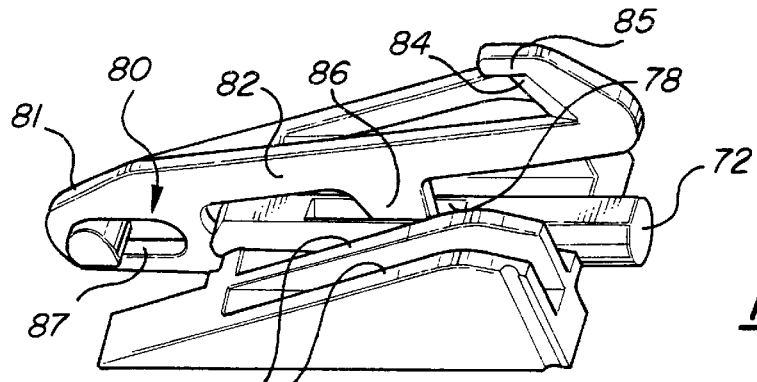
Figure 21:
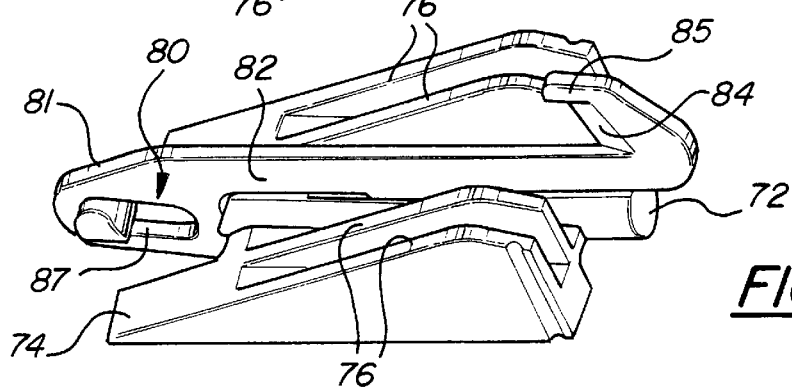

As noted, the preferred embodiment 10 is adapted to divide tissue between the stapled seams shortly after the seams have been formed. To this end, as shown in FIGS. 19–21, the sled 70 is provided with a cutting knife 80 which includes at its proximal end a cutting blade 84. The knife 80 extends through a longitudinal slot 69 formed in the shroud 56 such that blade 84 extends above the upper surface 52 thereof, as shown in FIG. 11. When jaws 42, 46 are in their closed position the extreme upper part of knife 80 extends into a slot 41 formed in anvil 46 shown in FIG. 10. Thus, as sled 70 travels distally through the cartridge 50, blade 84 also moves distally between the jaws 42, 46 cutting tissue clamped therebetween.

As shown in FIGS. 19–21, knife 80 is coupled to the sled 70 via a slot 87 in a leg 82 of the knife 80. Slot 87 allows the knife 80 to shift slightly forward (see FIG. 19) relative to the sled 70 and the cartridge 50 when a cartridge 50 is loaded so as to avoid interference between the knife 80 and the pivot pin 48 coupling jaws 42, 46 when a cartridge 50 is loaded. When the instrument 10 is fired, sled 70 initially moves a short distance in the distal direction until it engages the distal end of slot 87 (see FIG. 20). Thereafter, knife 80 will be pulled behind the ramped surfaces 74, 76 of sled 70 at a distance sufficient to ensure that the blade 84 will not divide tissue clamped between jaws 42, 46 until seams have been formed in the vicinity of the blade 84.

Since the blade necessarily is very sharp, the cartridge 50 preferably is designed to minimize risk of injury to persons handling the instrument. For example, as shown in FIG. 9, the shroud 56 of the cartridge 50 preferably is provided with a pair of safety projections 53. The safety projections 53 are disposed one on each side of the proximal end of the slot 69 in shroud 56 through which knife 80 extends. The safety projections 53 are spaced to accommodate passage of the projecting end of knife 80 so that when the knife 80 is in its proximal, unfired position the blade 84 is substantially shielded. Additionally, knife 80 is provided with a radiussed protrusion or overhang 85, as shown in FIG. 16, which extends beyond the blade 84. Thus, projections 53 and overhang 85 reduce the risk that operating personnel will be inadvertently injured when handling a new cartridge 50. Preferably, the instrument 10 is designed to reduce the risk of injury from a spent cartridge as well. Knife 80, therefore, is designed to pivot from a raised cutting position to a retracted position in which it is relatively inaccessible after firing. More particularly, knife 80 is pivotally coupled to sled 70 via the slot 87 at the distal end of knife leg 82. The leg 82 includes a follower 86 which extends through an opening 78 defined in the sled 70, as seen in FIGS. 19–21. Follower 86 rides against a grooved platform 59 disposed on the floor 68 of the cartridge housing 54 (see FIG. 9) as the sled 70 travels distally through the cartridge 50 during firing as illustrated in FIGS. 17–18. As shown in FIG. 16, the distal end of the leg 82 includes a tab 88 that engages the underside of the sled 70. Optionally, tab 88 could be located on the follower 86. Thus, follower 86 and tab 88 cooperate to maintain knife 80 in a raised, cutting position (see FIGS. 11 and 19) as the instrument 10 is fired.

However, as shown in FIG. 9, the grooved platform 59 has a slot 83 near its distal end. When the cartridge 50 is completely fired and the sled 70 nears its distal most position, the follower 86 falls through the slot 83, the knife 80 pivots downward (see FIG. 21), and the blade 84 falls through the slot 69 and into the central cavity of housing 54. To make sure that the knife 80 pivots into the central cavity, the distal end of the housing 54 is slanted downward and the distal end of the cutting knife 80 includes an angled surface 81 as shown in FIG. 16. The angled surface 81 of the knife 80 contacts the distal end of the housing 54 as the sled 70 completes its distal movement. The cooperation of those slanted surfaces forces the knife 80 to pivot into the housing 54 regardless of the orientation of the tip 40.

While incorporation of a knife is preferred, it is not an essential feature of the subject invention. For example, sled 70 may be replaced with an alternate sled 104 shown in FIG. 22. Sled 104 is similar to sled 70 except that it lacks a knife. It has, however, a wide leading camming surface and widely spaced trailing camming surfaces which can drive multiple rows of staple drivers in a manner and with benefits as described above in reference to sled 70.

Sled 70 also can be replaced with another alternate sled 105 shown in FIG. 23. Sled 105 is similar to sled 70 in many respects. However, unlike sled 70, sled 105 includes a visual indicator 106 at its distal end. The cartridge housing 54 may be provided with a suitable opening (not shown) at its distal end so that visual indicator 106 will extend out of the housing 54 when the sled 105 is in its most distal position. The user thus may be provided with a visual indication that a cartridge assembly 50 has already been fired.

The illustrated cartridge assembly 50 is preferred because it allows the surgeon to reliably, efficiently, and easily staple and divide tissue between the jaws. The advantages and features of the illustrated cartridge assembly are described in further detail in an application of Christopher L. Johnson, and David A. Dunlap, entitled Linear Stapling Instrument With Improved Staple Cartridge and filed concurrently herewith. The disclosure of that application is hereby incorporated by reference. It will be appreciated, however, that a variety of other cartridge assemblies are known and may be used when linear staplers are constructed in accordance with the subject invention. Obviously, such cartridge assemblies may be omitted entirely when other types of laparoscopic instruments are constructed. The incorporation and specific design of the staple cartridge is not part of the subject invention.

The laparoscopic instrument 10 is provided with a firing system 130 to drive the sled 70 from its proximal, unfired position to its distal, fired position. As shown in FIGS. 27–29, the firing system 130 includes the firing trigger 22 mentioned above, a firing rack 140, a gear train for converting the pivoting movement of the trigger 22 into a longitudinal movement of the rack 140, a firing tube 142, a firing rod 144, and a flexible drive cable 148.

As shown in FIG. 8, the trigger 22 is pivotally mounted upon a spindle 131 formed on the interior of the handle 20. It is biased towards its unfired position by one or both of a preloaded torsion spring 132 and an extension spring 138, as shown in FIGS. 33–36. A fixed arm 132b of the torsion spring 132 engages an extension of the interior wall of handle 20. The free arm 132a engages the end of a wall 139 located in the interior of trigger 22. The extension spring 138 extends between suitable posts near the bottom of the grip of handle 20 and on the trigger 22. Thus, in order to squeeze the trigger 22, a user must overcome the force of the torsion spring 132 and the extension spring 138, and once the firing stroke is completed, the trigger 22 automatically will return to its initial, unfired position.

Preferably, trigger 22 is provided with a feel which is comfortable to a surgeon. The force required to drive sled 70 as the cartridge 50 is fired obviously will contribute significantly to the feel of the trigger 22, and toward that purpose the firing force of cartridge 50 provides a favorable force profile. Consequently, the design of the trigger 22, torsion spring 132, and extension spring 138 preferably is coordinated to provide relatively uniform resistance across the entire stroke of the trigger 22.

It will be appreciated, therefore, that the trigger wall 139, when the trigger 22 is in its initial, unfired position, contacts the torsion spring 132 at a point well below the tip of spring arm 132a (see FIG. 33). Trigger 22 and spring arm 132a also pivot in opposite directions on separate pivot axes as the trigger 22 is operated. Consequently, as trigger 22 is pivoted inwardly from its initial position to commence firing, the contact point between trigger wall 139 and torsion spring 132 moves radially outward along spring arm 132a (see FIG. 36), and pivoting of the trigger 22 imparts decreasing movement to spring arm 132a. Those effects offset the increasing force required to move spring arm 132a.

Near the end of its stroke, however, continued pivoting of the trigger 22 imparts very little movement to the spring arm 132a. In this range of movement, therefore, torsion spring 132 offers very little resistance to pivoting of the trigger 22. Extension spring 138, however, offers increasing resistance as trigger 22 continues to pivot. That tends to compliment the decreasing resistance of torsion spring 132 near the end of the trigger stroke, and the overall effect is to provide more uniform resistance throughout the entire stroke of the trigger 22.

The trigger 22 includes a pair of integrally formed arcuate gear racks 134. The rotation of the trigger 22 about the spindle 131 causes a similar rotational movement of the arcuate gear racks 134. As best appreciated from FIGS. 8 and 33–36, the arcuate gear racks 134 mesh with two pairs of gear teeth 133 which are attached to a gear 137. The compound gear assembly 135 of gears 133, 137 is pivotally mounted on another spindle 136 formed on the interior of the handle 20 such that gear teeth 137 mesh with the rack 140. Thus, when a user squeezes the trigger 22 towards the handle 20, the arcuate gears 134 cause the compound gear 135 to rotate which, in turn, drives the rack 140 distally thereby converting the rotational or pivoting movement of the trigger 22 into longitudinal movement of the rack or driver 140.

As in the jaw closure system 89 and the articulation control system 110 described above, the firing system 130 is adapted to accommodate rotation of the shaft 30 relative to the handle 20. To this end, the distal end of the rack or driver 140 is rotatably coupled to the proximal end of the driver tube 142, as can be seen from FIGS. 27 and 33–36. As in the jaw closure and articulation control systems 89, 110, this rotatable engagement is implemented by providing an annular trough 141 in the outer surface of the substantially cylindrical distal end of the rack 140 and a pair of opposed tabs 143 formed in the proximal end of the firing tube 142. The trough 141 and tabs 143 secure the firing tube 142 and the driver or rack 140 together while permitting relative rotation between these two components. This arrangement permits the driver 140 to transfer its longitudinal motion to the firing tube 142 while simultaneously permitting relative rotation between the portions of the firing system 130 disposed in the shaft 30 and the portions disposed in the handle 20.

The distal end of the firing tube 142 is fixedly attached to the proximal end of the firing rod 144 as shown in FIG. 27. This firing rod 144 is rigid, and thus, longitudinal movements of the firing tube 142 are reflected in corresponding movements of the firing rod 144.

The distal end of the firing rod 144 is fixedly attached to the flexible cable 148. The flexible cable 148 extends from the distal end of the firing rod 144, through the articulation joint, into the tip 40 of the instrument 10, and ultimately abuts against the sled 70. Thus, distal motion of the cable 148 drives the sled 70 distally through the cartridge 50 firing the cartridge 50 as described above. Moreover, since the cable 148 is flexible and can bend at the articulation joint, the instrument 10 may be fired when the tip is articulated.

Since cable 148 is flexible, the shaft 30 and tip 40 assemblies preferably provide lateral support for the cable 148 to prevent it from buckling and to more efficiently and reliably transmit force from the firing rod 144 to the sled 70. Accordingly, as shown in FIGS. 27–29, the flexible cable 148 passes through a groove which extends along the bottom of the U-shaped channel in clevis body insert 33. The groove closely accommodates cable 148, and insert 33 accommodates camming driver 94 over the groove. The insert 33 extends longitudinally close to, and the camming driver 94 extends beyond the articulation axis. Thus, cable 148 is laterally constrained within the groove and bending of the cable within the shaft 30 is minimized.

Similarly, the tip 40 includes a receiver insert 108, as shown in FIGS. 28–29, which is disposed near the proximal end of receiver 42 between the cartridge 50 and the articulation joint. The cable 148 passes through a bore in the receiver insert 108. The cable 148 then passes through a bore in the cartridge shroud 56 and into the groove in platform 59 of cartridge floor 68 (see FIG. 9). Those bores and grooves are sized to closely accommodate the flexible cable 148, thereby laterally constraining it and minimizing flexing of the cable 148 in the tip 40.

As best appreciated by comparing FIGS. 28–29, the camming driver 94, when it is in its distal, clamping position, extends from the distal end of the clevis body insert 33, through the articulation joint, and onto the top surface of the proximal end of the receiver insert 108. The proximal end of the receiver 42 extends through the articulation joint and under the lower surface of clevis body insert 33. The cable 148 passes therebetween, and thus, it will be appreciated that it is substantially constrained from bending out of the plane of articulation.

Necessarily, however, the cable 148 must bend in the plane of articulation when the tip 40 is articulated. Such bending invariably increases to some degree the tendency of a cable to buckle, the resistance of a cable to movement through the articulation joint, and the tendency of the tip to straighten when force is transmitted through the cable. Accordingly, in instrument 10 cable 148 passes through a flexible guide 145 which extends generally between the clevis body insert 33 in shaft 30 and the receiver insert 108 on receiver 42.

The proximal portion 145a of guide 145, as best seen in FIG. 28, is elongated and has a generally U-shaped cross-section with lips extending perpendicular from the sidewalls thereof. The proximal portion 145a of the guide 145 is accommodated in the distal end of the groove in clevis body insert 33. The groove has adjoining recesses which accommodate the side lips of guide 145 such that the upper surface thereof is flush with the surface of the clevis body insert 33. A pair of arms 145b extend from the sides of the proximal portion 145a of the guide 145 distally through the articulation joint. The arms 145b terminate in hooks 145c which are received in a shallow, rectilinear well 109 in receiver 42.

The arms 145b are relatively thin, elongated rectilinear members having a length which extends in the plane of articulation and a width which extends perpendicular thereto. The width of the arms 145b is large relative to the diameter of the cable 148, preferably at least as wide as the cable diameter. Thus, the arms 145b are flexible and provide support for the cable when the tip 40 is articulated. In accordance therewith, the arms 145b, when the tip is in its aligned or unarticulated position, are adjacent to the cable 148 to minimize any play in the cable 148 which otherwise might exist.

Furthermore, the length of well 109 in receiver 42 are oversized relative to arm hooks 145c. As the instrument 10 articulates, therefore, hooks 145c can slide longitudinally within well 109, thereby allowing the guide arms 145b to bend, each independently of the other, in a concentric fashion. Thus, binding of the cable between the arms 145b is avoided. Preferably, the well 109 is sized so that, when the tip 40 is fully articulated, the hook 145c of the guide arm 145b having the larger radius engages the proximal end of well 109 to impart to the arm 145b a uniform bend which is inscribed by the angle of articulation. In this manner, the arms 145b will provide rigid support for the cable 148 over a like bend and will preclude any buckling of the cable 148 in the plane of articulation.

It will be appreciated, of course, that since the ends of the guide arms 145b are slidably engaged with receiver 42, that the arms 145b may not prevent all buckling of cable 148. When the tip is less than fully articulated, the arms 145b may slide and permit cable 148 to buckle somewhat until the hooks 145c engage the proximal end of well 109. At the same time, however, it will be appreciated that the arms 145b allow progressively less buckling of cable 148 as it is increasingly articulated and, thus, is increasingly susceptible to buckling.

It also will be appreciated, therefore, that the guide 145 serves to impart a more uniform bend to cable 148 as the tip 40 is articulated. The guide 145 also provides a smooth surface over which cable 148 may travel in passing out of the shaft 30 and into the tip 40. Thus, the guide 145 helps to reduce the resistance of cable 148 to movement through the articulation joint, and correspondingly, reduces the force required to fire the instrument 10. The guide 145 also helps to inscribe the bending of cable 148 within the angle of articulation. To the extent that is accomplished, the guide 145 helps to minimize moments which tend to move the tip 40 when the instrument 10 is fired in an articulated position.

As noted above, cable 148 abuts sled 70 when the sled 70 is in its proximal most, loaded position. More precisely, cable 148 abuts sled 70 on a proximally facing bearing surface 72. Thus, when a user squeezes trigger 22, thereby driving cable 148 forward, cable 148 will drive the sled 70 distally through the cartridge 50. The cable 148, however, is not hooked or otherwise attached to the sled 70. Consequently, when trigger 22 is released and the firing system 130, including cable 148, returns to its unfired position, sled 70 remains in its distalmost position and, more importantly, knife 80 remains in its retracted position. If a user attempts to refire a previously fired cartridge, therefore, the knife 80 is incapable of severing unstapled tissue.

It should be noted that, when the jaw closure system 89, the articulation control system 110, and the firing system 130 are all incorporated into the same instrument 10, the clamp-up driver 90, the clamp-up tube 92, the articulation driver 112, the articulation tube 116, the firing rack 140, and the firing tube 142 preferably all are elongated, substantially cylindrically-shaped tubes or rods which are more or less concentrically disposed relative to the shaft 30 as shown. More particularly, the clamp-up driver 90 and the clamp-up tube 92 are preferably chosen to fit within the articulation driver 112 and the articulation tube 116, respectively, and the firing rack 140 and the firing tube 142 are chosen to fit within the clamp-up driver 90 and the clamp-up tube 92, respectively, as shown in FIGS. 33–36. The bottom half of the proximal portion of clamp-up driver 90 and articulation driver 112 is cut away to allow the compound gear 135 to pass therethrough and engage the firing rack 140. Similarly, an opening is provided in the upper portion of the articulated driver 112 so that lever 28 can be coupled to clamp-up driver 90.

Thus, not only is space within the instrument efficiently utilized, but the shaft 30 assembly may be easily sealed to prevent the passage of gas and body fluids. For example, as shown in FIG. 8, elastic annular seals 120a, 120b, and 120c are disposed around, respectively, firing rack 140, clamp-up driver 90, and articulation driver 112 in annular seats provided therein. A silicone or other type of sealant/lubricant may be added in this area. Other methods of sealing the shaft are known, however, and may be used if desired.

The illustrated firing system 130 is preferred because it allows the surgeon to reliably, efficiently, and easily generate the force necessary to fire the cartridge 50. The advantages and features of the illustrated firing system are described in further detail in an application of Jeffrey R. Oberlin, Christopher L. Johnson, and David A. Dunlap, entitled Articulated Surgical Instrument With Improved Firing System and filed concurrently herewith. The disclosure of that application is hereby incorporated by reference. It will be appreciated, however, that a variety of other firing systems are known and may be used when linear staplers are constructed in accordance with the subject invention. Obviously, such firing systems may be omitted entirely when other types of laparoscopic instruments are constructed. The incorporation and specific design of the firing system is not part of the subject invention.

Instrument 10 preferably is designed to minimize accidental misoperation of the instrument. Accordingly, instrument 10 also includes a passive Lockout system and an active lockout system. The passive lockout system immobilizes the firing system 130 when the jaws 42, 46 are in their open position, but allows operation of the firing system 130 when the jaws 42, 46 are closed. The active lockout system immobilizes the firing system 130 until it is manually released by a surgeon. Together, the active and passive lockout systems reduce the risk that instrument 10 will be fired when the jaws 42, 46 are not properly closed or positioned.

More specifically, instrument 10 comprises a passive lockout system which includes a pivoting key 152 shown in FIG. 8 which interacts with the clamp-up lever 28 and the link 150. As noted above, clamp-up lever 28 actuates the jaw closure system 89 and closes jaws 42, 46. As discussed above, link 150 serves to couple the clamp-up lever 28 to the handle 20 so that pivoting of the clamp-up lever 28 from its raised, open position to its lowered, closed position moves the clamp-up driver 90 distally. Clamp-up lever 28, however, through link 150 passively actuates key 152 such that key 152 immobilizes the firing system 130 unless the jaws 42, 46 are closed.

More particularly, as best seen in FIGS. 33–36, link 150 is a generally V-shaped member having a distal arm and a pair of opposed proximal arms extending therefrom. The proximal arms of link 150 have arcuate slots 157 near their ends. Link 150 is pivotally coupled to both the handle 20 and the clamp-up lever 28 via pins 151 as described above.

Pivoting key 152 is a generally L-shaped member having a proximal arm and a distal arm 154. The proximal arm of pivoting key 152 is pivotally coupled near its end to the handle 20 by posts 153 which extend into suitably configured blind bores in handle halves 25, 27. Key 152 also has a pair of posts 158 located near the intersection of its proximal and distal 154 arms which extend through slots 157 in link 150, thereby pivotally coupling key 152 to link 150.

Figure 34:
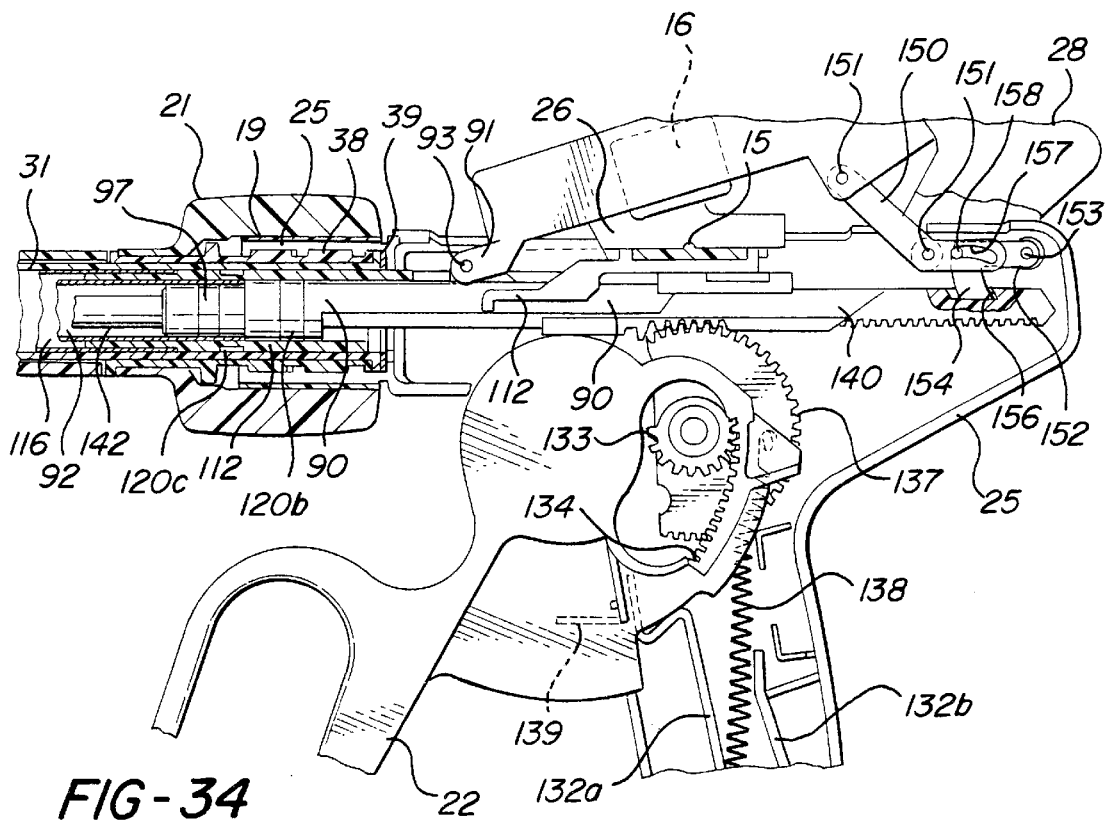
FIGS. 33–36 are a left side elevational views of the handle 20 of instrument 10, certain components thereof being removed, partially torn away, or cross sectioned along line 33—33 of FIG. 6, showing in particular the passive lockout system, the trigger springs 132, 138, and various drive members in the handle 20 and shaft 30 assemblies.
Figure 33:
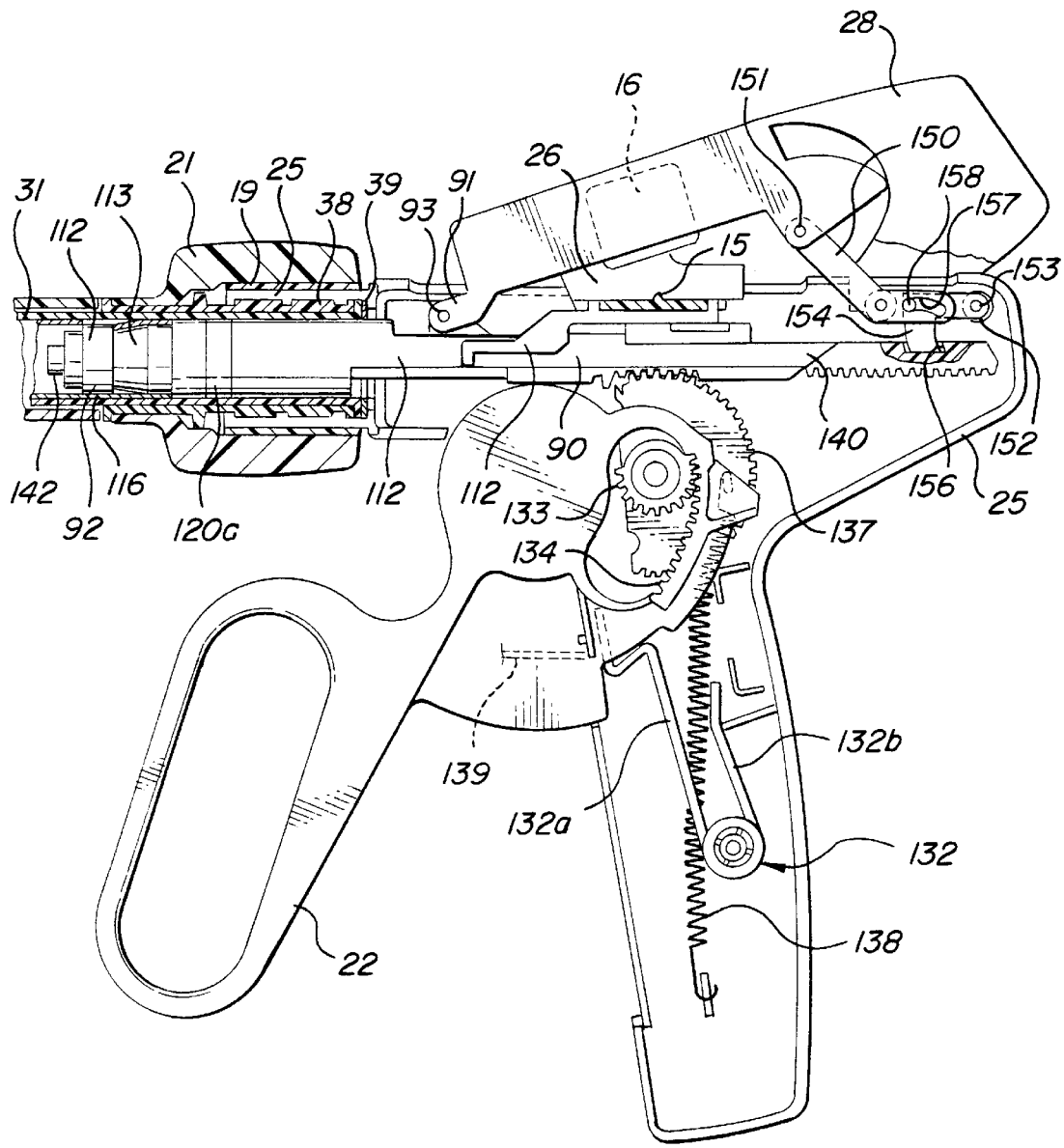

Consequently, when the clamp-up lever is in its raised position (the open-jaw position), link 150 locates key 152 in a lower position as shown in FIGS. 33–34. When key 152 is in its lower position, its distal arm 154 extends downward and engages a notch 156 formed in the upper surface of firing rack 140. Thus, rack 140 cannot move distally, and the instrument 10 cannot be fired when jaws 42, 46 are open.

Figure 35:
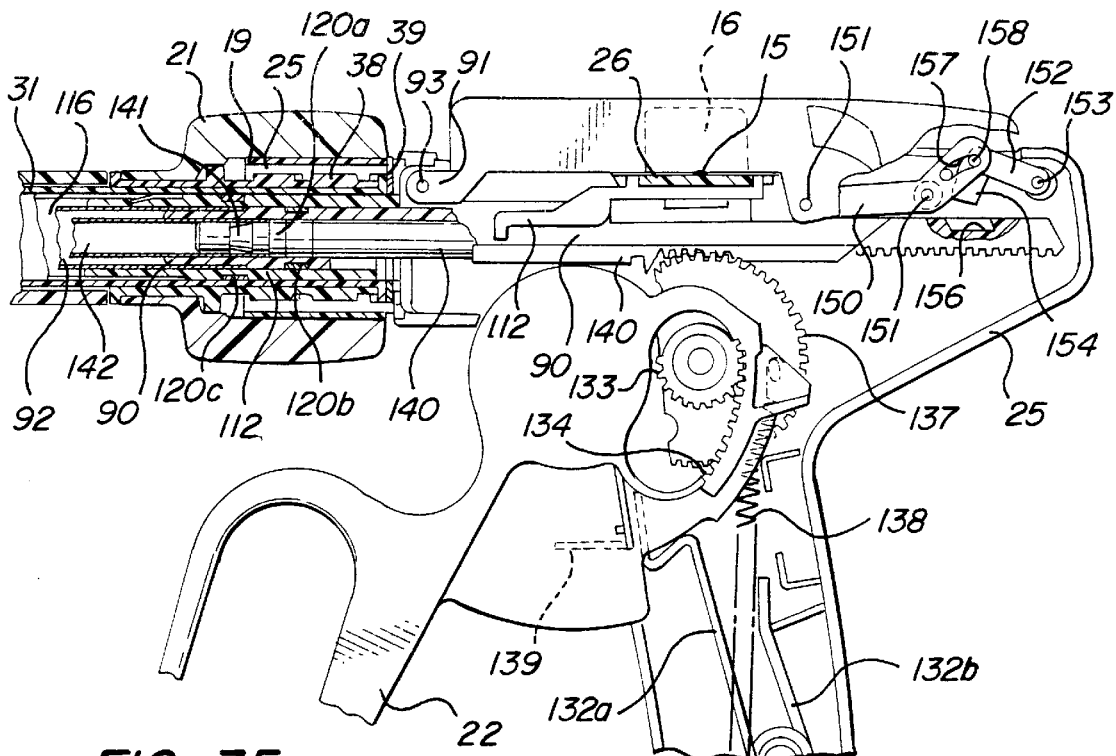
Figure 36:
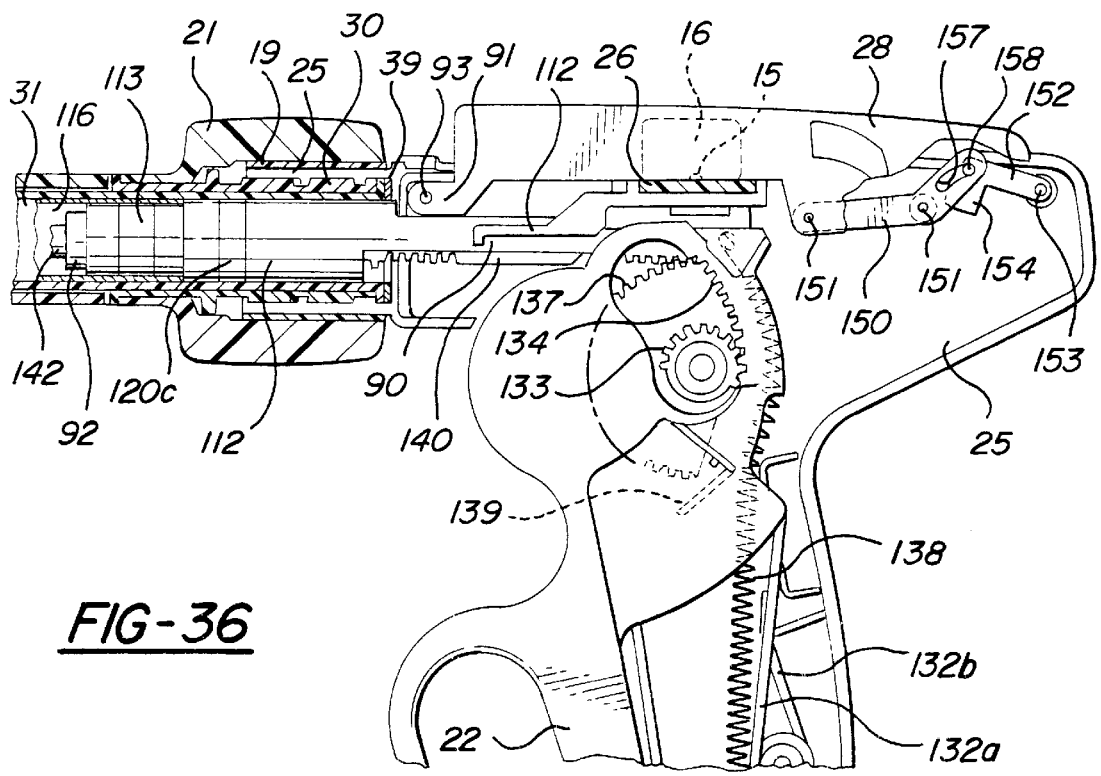

When jaws 42, 46 are closed by moving clamp-up lever from its raised to its lowered position (the closed-jaw position), link 150 causes key 152 to pivot upward as shown in FIG. 35. As key 152 pivots upward, the distal arm 154 likewise pivots out of engagement with rack notch 156. Thus, key 152 no longer prevents rack 140 from moving distally and the instrument 10 from being fired (see FIGS. 35–36) as described in detail above. It will be appreciated, however, that by virtue of slots 157 pivoting of key 152 is delayed somewhat relative to pivoting of clamp-up lever 28 and link 150. The proximal edge of the distal arm 154 of key 152 also is arcuate shaped. Together, the delayed pivoting of key 152 and the arcuate edge of its distal arm 154 ensures that the distal arm 154 of key 152 will remain engaged with rack notch 156 until near the end of the lever stroke and until the jaws 42, 46 are fully closed.

Figure 37:
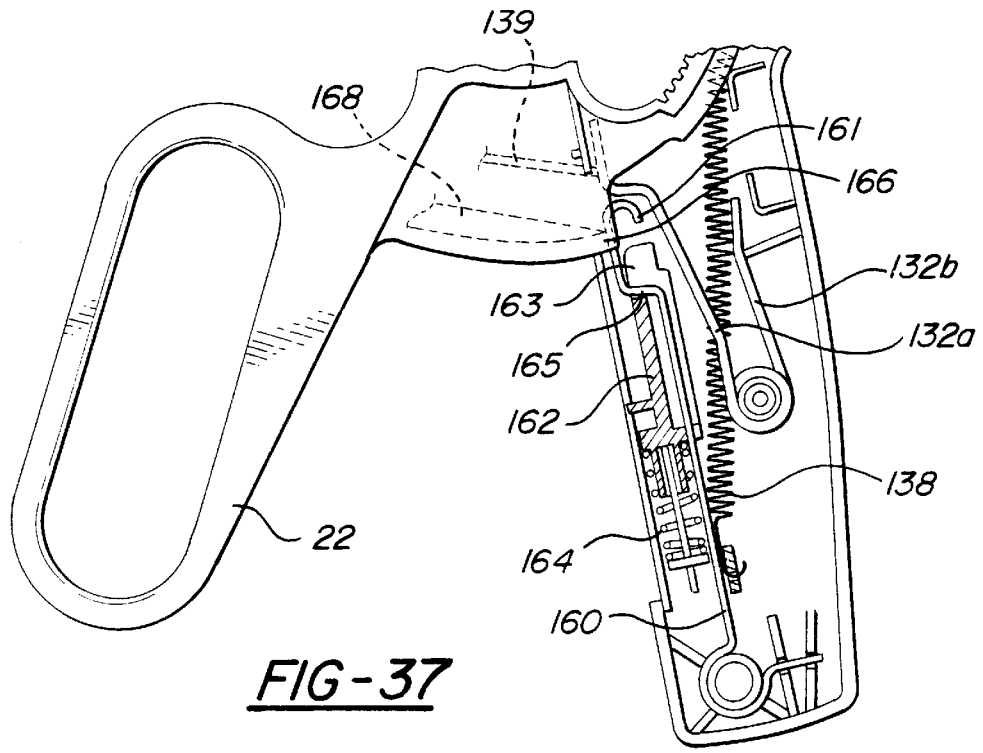
FIG. 37 is a left side elevational, partial view of the handle assembly 20 of instrument 10, certain components thereof being removed or cross-sectioned as in FIGS. 33–36, showing in particular the active lockout system.

Instrument 10, in accordance with preferred aspects of the invention, comprises an active lockout system which includes the safety switch 24 previously noted, a plunger 162, a compression spring 164, and a latch 160 shown in FIG. 8 which interact with the trigger 22. The switch 24 is slidably mounted on the exterior distal side of the grip of handle 20 so that it can be easily manipulated by a surgeon, as best seen in FIGS. 1–3. Preferably, bosses 23 are provided on each side of the switch 24 to facilitate manipulation of the switch 24 by the thumb (either left or right) of a surgeon. The switch 24, as shown in FIG. 37, is coupled to plunger 162 which is slidably mounted within an appropriate track 169 (see FIG. 8A) formed on the inside of handle 20. Compression spring 164 biases plunger 162 and switch 24 towards a raised, normal position.

Figure 38:
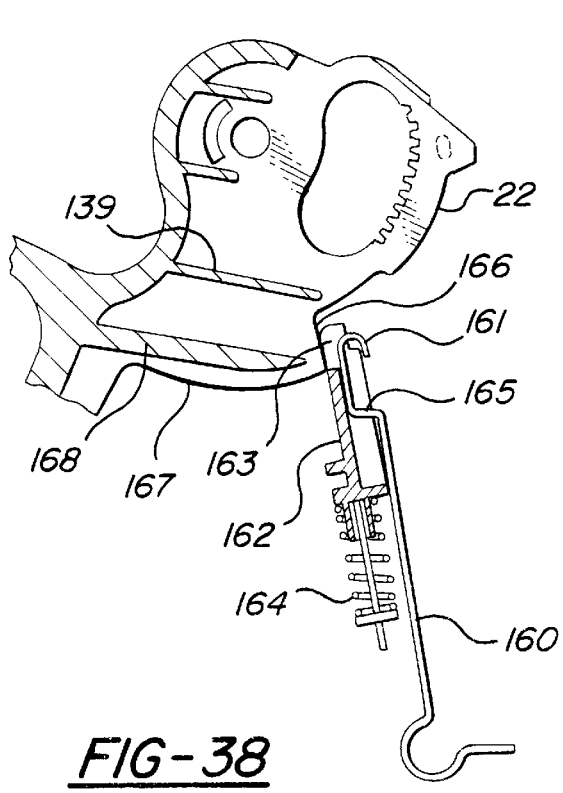
FIGS. 38–42 are cross-sectional views taken generally along line 33—33 of FIG. 6 of the active lockout assembly and trigger in handle assembly 20 of instrument 10 showing those components in various positions.

In its normal, activated position, the upper end of plunger 162 extends into notch 166 formed in the arcuate bottom surface 167 of trigger 22 as shown in FIG. 38. Plunger 162 thereby prevents trigger 22 from pivoting and the instrument 10 from being fired. That is, if the trigger 22 is urged toward the handle 20, the rear surface of notch 166 will abut the forward surface of the upper end of plunger 162.

Latch 160, as shown in FIG. 37, has a fixed arm restrained near the bottom of handle 20. Its free arm extends upwards and terminates in a hook-shaped tip 161 which is offset from the rest of the free arm by a transverse section 165. The latch 160 is preloaded such that its free arm is biased in the distal direction.

Figure 39:
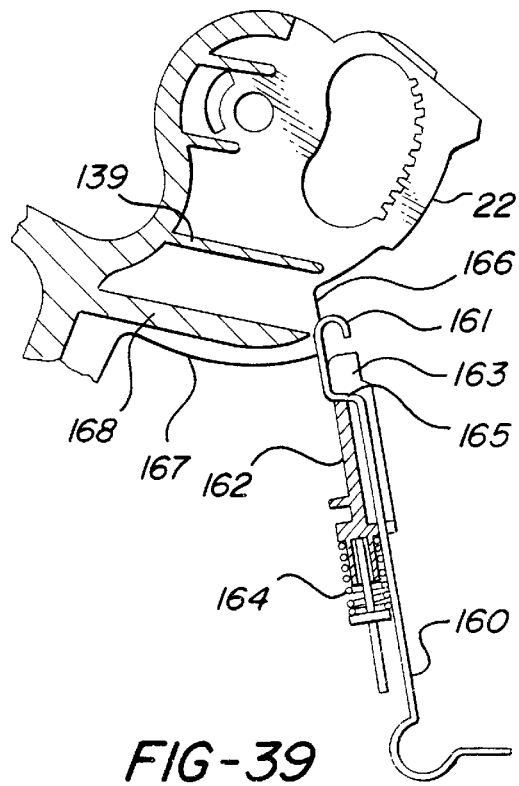

When plunger 162 is in its raised, normal position shown in FIG. 38 (compare switch 24 in FIG. 1), latch tip 161 bears on the back surface of plunger 162, the upper end of which plunger 162 as noted engages trigger notch 166. When the switch 24 is slid downward by a surgeon, plunger 162 likewise moves downward and out of engagement with trigger notch 166. At this point, as shown in FIGS. 37 and 39, the latch tip 161 passes through a vertical slot 163 formed in the end of plunger 162. The latch tip 161 in this position extends into trigger notch 166 and bears on a contact rib 168 in trigger 22 which terminates at notch 166.

When the switch 24 is released, the bottom surface of plunger slot 163 bears against the transverse section 165 of the free arm of latch 160. Latch 160 thereby engages plunger 162 and holds it in a lowered, disengaged position where it does not block trigger 22 from pivoting (compare switch 24 in FIG. 2). Assuming that the jaws 42, 46 have been clamped shut to disengage the passive lockout system described above, the trigger 22 now can be actuated to fire the instrument 10.

Figure 40:
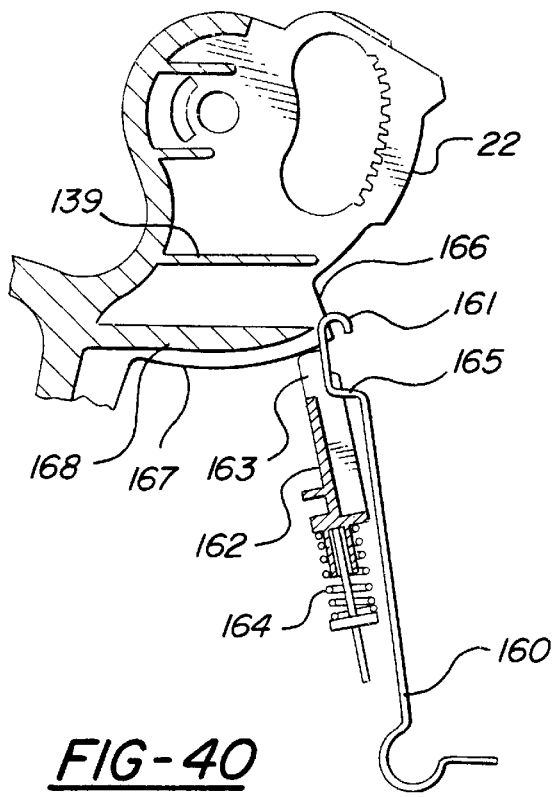
Figure 41:
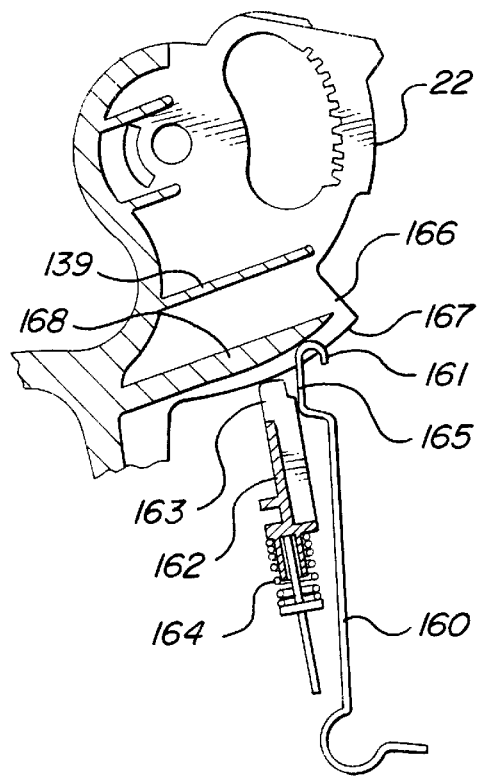

As trigger 22 pivots in firing the instrument 10, the contact rib 168 provides a camming surface which bends latch tip 161 back out of the slot 163 in the end of plunger 162 as shown in FIGS. 40–41. The plunger 162, therefore, is no longer restrained by latch tip 161 and is free to move upwards. Since trigger notch 166 has pivoted out of alignment with the plunger 162, however, plunger 162 shifts slightly upward to an intermediate position in which its top surface bears on the arcuate lower edges 167 of trigger 22 (compare switch 24 in FIG. 3).

Figure 42:
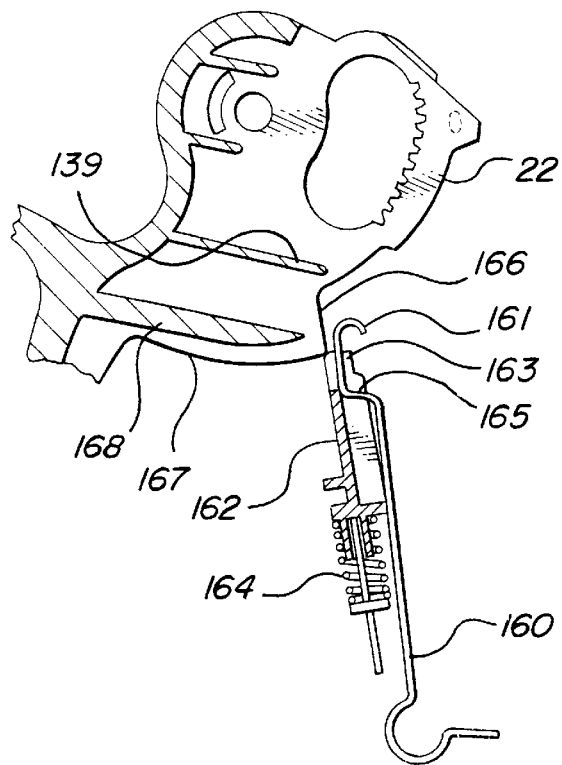

When plunger 162 is in its intermediate position, the slot 163 in its end is no longer aligned with the latch tip 161. Consequently, when the instrument has been fired and trigger 22 is pivoted back to its starting position, latch tip 161 ultimately again comes to rest against the back of plunger 162, as shown in FIG. 42, instead of passing back through the slot 163. Plunger 162, therefore, is free to move back to its normal, raised position in which it engages trigger notch 166, as shown in FIG. 38, and trigger 22 is immobilized until switch 24 is manually actuated again.

The illustrated lockout systems are preferred because, though relatively simple in design, they significantly reduce the likelihood that a surgeon will fire a cartridge before the jaws are properly positioned and clamped over tissue. More particularly, the active lockout system automatically resets after each actuation of the firing trigger. There is no need for a surgeon to manually reset the trigger safety. Further, each time the instrument is used to perform the surgical operation the jaws of the instrument must be closed and the active lockout switch must be actuated. Otherwise, the firing system of the instrument is immobilized by one or both of the passive and active lockout systems. The risk that the instrument will be inadvertently fired, therefore, is reduced.

The advantages and features of the illustrated lockout systems are described in further detail in an application of Lars R. Chrisman, Scott H. Heneveld, and Stephen F. Peters, entitled Surgical Instrument With Improved Safety Lockout Mechanisms and filed concurrently herewith. The disclosure of that application is hereby incorporated by reference. It will be appreciated, however, that a variety of other lockout systems are known and may be used when linear staplers are constructed in accordance with the subject invention. Obviously, such lockout systems may be omitted entirely if desired, especially when other types of instruments are constructed. The incorporation and specific design of the lockout system is not part of the subject invention.

In general, the components of the novel instruments may be fabricated from conventional materials by methods well known to workers in the art. For example, the outer tube 31 of the shaft assembly 30 preferably is constructed of aluminum. The jaws 42, 46 may be fabricated from steel. Parts such as the firing rod 144 and camming driver 94 which are subject to relatively high stress per unit area preferably are fabricated from higher strength materials such as steel. Parts may be fabricated from steel to produce thinner or smaller parts, and so, the firing tube 142, the clamp-up tube 92, and articulation tube 116 preferably are fabricated from thin-walled steel tubing. Other parts which are subject to low stress or which distribute high stresses over a larger area may be fabricated from structural plastics. For example, space constraints are not as great in the handle as they are in the shaft, and thus, the firing rack 140, the clamp-up driver 90, and the articulation driver 112 preferably are fabricated from plastics and have thicker cross-sections. Exterior parts, such as the handle 20 and rotation knob 21, for aesthetic reasons preferably have a smooth, shiny finish, and thus, preferably are molded from polycarbonates. Interior plastic components, where aesthetics are less of a concern and mechanical properties are more important, in general may be fabricated from polyamides such as nylon. A variety of structural plastics are known and may be used in fabricating components of the novel instruments.

As will be readily appreciated by those working in the art, the various components of the novel instruments may be provided with a wide variety of bosses/recesses, pins/openings, and other types of mating or complimentary surface features which facilitate assembly or discourage misassembly of the instrument. In general, however, to simplify the illustration and explication of the preferred embodiment such aspects in general are not shown in the drawings, nor are they always discussed specifically.

In use, a surgeon first inserts the closed jaws 42, 46 and the shaft 30 of the illustrated linear stapler 10 through a cannula. After opening the jaws 42, 46, the surgeon manipulates the articulation slide control 26 and the rotation knob 21 to position the open jaws 42, 46 about the tissue to be stapled and cut. The surgeon then pivots the clamp-up lever 28 downward to clamp the jaws 42, 46 around the tissue. Once the jaws 42, 46 are clamped over the appropriate tissue, the passive lockout system is disengaged, but the active lockout system remains engaged and the instrument 10 still cannot be fired. Consequently, the surgeon actuates the safety switch 24 to activate the instrument 10. At that point the surgeon squeezes the trigger 22 to staple and cut the clamped tissue. The safety switch 24 automatically reactivates. The surgeon then unclamps the tissue, closes the jaws 42, 46, straightens the tip 40, and withdraws the instrument 10 from the cannula. If necessary, the surgeon replaces the spent cartridge 50 with a new one, and repeats the procedure.

Although the invention has been described in connection with certain embodiments, it will be understood that there is no intent to in any way limit the invention to those embodiments. On the contrary, the intent is to cover all alternatives, modifications and equivalents included within the spirit and scope of the invention as defined by the appended claims.

We claim:

1. An articulated surgical instrument for use in laparoscopic surgical procedures comprising:

a handle;

an elongated shaft having a distal end and a proximal end, said proximal end of said elongated shaft being coupled to said handle;

a tip pivotally coupled to said distal end of said shaft for articulation about an articulation axis and including two opposed jaws pivotally coupled at a pivot axis for movement between an open position and a closed position, at least one of said jaws having a camming portion proximal to said pivot axis of said jaws; and a camming driver disposed in said shaft for reciprocating movement between a proximal position and a distal position and including a camming portion which contacts said jaw camming portion such that movement of said camming driver from its proximal position to its distal position causes said jaws to pivot from their open position to their closed position;

wherein said jaw camming portion and said driver camming portion are adapted to contact each other at a cam point thereby accommodating articulation of said tip.

2. The surgical instrument of claim 1, wherein one of said camming portions defines a curved surface and the other said camming portion defines a planar surface.

3. The surgical instrument of claim 2, wherein said curved surface is a truncated spherical surface.

4. The surgical instrument of claim 1, wherein said jaw camming portion defines a curved surface and said driver camming portion defines a planar surface.

5. The surgical instrument of claim 1, wherein said jaw camming portion defines a truncated spherical surface and said driver camming portion defines a planar surface.

6. The surgical instrument of claim 1, wherein one of said camming portions is a hemispherically shaped projection and the other said camming portion is a ramp.

7. The surgical instrument of claim 1, wherein said jaw camming portion is a hemispherically-shaped projection and said driver camming portion is a ramp.

8. The surgical instrument of claim 1, wherein said cam point is located proximate to said articulation axis.

9. The surgical instrument of claim 1, wherein said jaw camming portion is a projection having a curved surface which has an axis of symmetry proximate to said articulation axis.

10. The surgical instrument of claim 1, wherein said jaw camming surface portion is a hemispherically-shaped projection having a center proximate to the articulation axis.

11. The surgical instrument of claim 1, wherein said instrument is a linear stapler having a removable staple cartridge and said jaws include a receiver adapted to removably receive the staple cartridge and an anvil.

12. The surgical instrument of claim 1, wherein one of said jaws pivots relative to the other of said jaws during closure of said jaws.

13. The surgical instrument of claim 1, wherein said anvil pivots relative to said receiver.

14. The surgical instrument of claim 1, wherein one of said jaws is pivotally coupled to said distal end of said shaft for articulation and wherein the other said jaw is pivotally coupled to said distal end of said shaft for articulation and is pivotally coupled to said one of said jaws for pivoting movement relative thereto.

15. The surgical instrument of claim 1, wherein said instrument further comprises:

a manually operable actuator mounted on said handle; and a drive shaft operatively coupled to said actuator and disposed in said handle for reciprocating movement between a proximal position and a distal position in response to actuation of said actuator and operatively coupled to said camming driver such that reciprocating movement of said drive shaft is transferred to said camming driver.

16. The surgical instrument of claim 15, wherein said manually-operable actuator comprises a lever which is moveable between a raised position corresponding to said proximal position of said drive member and a lowered position corresponding to said distal position of said driver member.

17. The surgical instrument of claim 16, wherein said lever has a distal end pivotally connected to said drive shaft and a proximal end pivotally connected to said handle by a pivoting link.

18. The surgical instrument of claim 15, wherein said drive shaft is an elongated, cylindrically-shaped tube.

19. The surgical instrument of claim 1, wherein said camming driver is a elongated shaft having a camming surface at a distal end thereof.

20. The surgical instrument of claim 1, wherein said instrument further comprises:

a manually operable actuator mounted on said handle;

a first drive shaft coupled to said actuator and disposed in said handle for reciprocating movement between a proximal position and a distal position in response to actuation of said actuator; and a second drive shaft coupled to said first drive shaft for rotation relative thereto and disposed in said elongated shaft for reciprocating movement between a proximal position and a distal position in response to reciprocating movement of said first drive shaft; wherein said camming driver is operatively coupled to said second drive shaft such that reciprocating movement of said second drive shaft is transferred to said camming driver.

21. In an articulated surgical instrument for use in laparoscopic surgical procedures including a handle; an elongated shaft having a distal end and a proximal end, the proximal end of the elongated shaft being coupled to the handle; a tip pivotally coupled to the distal end of the shaft for articulation about an articulation axis and including two opposed jaws pivotally coupled at a pivot axis for movement between an open position and a closed position; a manually engageable actuator mounted on the handle; and a drive shaft operatively coupled to the actuator which reciprocates between a proximal position and a distal position in response to movements of the actuator; the improvement comprising:

at least one of the jaws having a camming portion proximal to the pivot axis of the jaws; and a camming driver coupled to the drive shaft and disposed in the elongated shaft for reciprocating movement between a proximal position and a distal position in response to the reciprocating movement of the drive shaft, said camming driver having a camming portion which contacts said jaw camming portion such that movement of said camming driver from its proximal position to its distal position causes the jaws to pivot from their open position to their closed position;

wherein said jaw camming portion and said driver camming portion are adapted to contact each other at a cam point thereby accommodating articulation of the tip.

* * * * *